(12) United States Patent
Stark et al.

(10) Patent No.: US 6,296,595 B1
(45) Date of Patent: *Oct. 2, 2001

(54) METHOD OF OPTIMIZING ISOMETRIC EXERCISE

(75) Inventors: John G. Stark, Deephaven; Richard G. Lund, Crystal; Cecil H. Nelson, Chanhassen; Brynn D Rogers, Minneapolis, all of MN (US)

(73) Assignee: IZEX Technologies, Inc., Golden Valley, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 08/520,802

(22) Filed: Aug. 30, 1995

Related U.S. Application Data

(63) Continuation of application No. 08/298,591, filed on Aug. 31, 1994, now Pat. No. 5,484,389, which is a continuation of application No. 07/733,207, filed on Jul. 19, 1991, now Pat. No. 5,368,546, which is a continuation of application No. 07/483,139, filed on Feb. 21, 1990, now Pat. No. 5,052,375.

(51) Int. Cl.$^7$ ................................................. A63B 21/002
(52) U.S. Cl. ................................... 482/91; 482/8; 601/34
(58) Field of Search ................................. 601/23, 33, 34; 128/774, 782; 73/379.01, 329.04, 379.06; 482/91, 8

(56) References Cited

U.S. PATENT DOCUMENTS

| | | |
|---|---|---|
| 3,374,675 | 3/1968 | Keropian . |
| 3,929,335 | 12/1975 | Malick . |
| 4,037,480 | 7/1977 | Wagner . |
| 4,306,571 | 12/1981 | McLeod, Jr. . |
| 4,436,099 | 3/1984 | Raftohoulos . |
| 4,501,148 | 2/1985 | Nicholas et al. . |
| 4,553,124 * | 11/1985 | Malicki ................................. 338/5 |

(List continued on next page.)

OTHER PUBLICATIONS

Lieb et al., The Journal of Bone and Joint Surgery, vol. 53–A(4), pp. 749–758.

Knapik, J. et al., Angular Specificity and Test Mode Specificity of Isometric and Isokinetic Strength Testing, The Journal of Orthopedic and Sports Physical Therapy, vol. 5, No. 2, pp. 58–65 (1983).

(List continued on next page.)

*Primary Examiner*—Mickey Yu
*Assistant Examiner*—Benjamin K. Koo
(74) *Attorney, Agent, or Firm*—Westerman, Champlin & Kelly; Peter S. Dardi

(57) ABSTRACT

An instrumented orthopedic restraining device is provided. The device includes an ambulatory housing, including first and second distal end portions, and restraining means for restraining movement of the first and second distal end portions relative to one another. The restraining device preferably includes an elongated restraining bar equipped with a stress sensing mechanism for sensing stress on the restraining bar. A control unit is provided for indicating sensed stress based upon outputs from the stress sensing mechanism. Preferred embodiments include a plurality of strain gauges attached to the elongated restraining bar and interconnected with the control unit which preferably includes a recording mechanism and a microprocessor mechanism. The elongated restraining bar alternately includes an adjustable hinge interconnecting distal end sections of the elongated restraining bar, wherein the angle between the respective distal end sections can be adjusted relative to one another. The adjustable hinge is preferably an electromechanical hinge which can be at least partially controlled by software read by the microprocessor mechanism. Methods of using embodiments of the present invention are also disclosed.

1 Claim, 10 Drawing Sheets

U.S. PATENT DOCUMENTS

| | | |
|---|---|---|
| 4,576,158 | 3/1986 | Boland . |
| 4,586,495 | 5/1986 | Petrofsky . |
| 4,604,098 * | 8/1986 | Seamone et al. ................... 623/60 |
| 4,624,246 | 11/1986 | Ajemian . |
| 4,681,097 | 7/1987 | Pansiera . |
| 4,697,808 * | 10/1987 | Larson et al. ..................... 482/51 |
| 4,718,665 | 1/1988 | Airy et al. . |
| 4,763,901 | 8/1988 | Richter . |
| 4,848,152 | 7/1989 | Pratt, Jr. . |
| 4,905,560 | 3/1990 | Suzuki et al. . |
| 4,909,262 * | 3/1990 | Halpern et al. ................... 128/774 |
| 4,912,638 | 3/1990 | Pratt, Jr. . |
| 4,913,163 * | 4/1990 | Roger et al. ..................... 128/782 |
| 4,928,959 | 5/1990 | Bassett et al. . |
| 4,944,288 * | 7/1990 | Rawcliffe ........................ 601/33 |
| 5,050,618 * | 9/1991 | Larsen ........................... 128/774 |
| 5,052,379 * | 10/1991 | Airy et al. ........................ 602/16 |
| 5,078,152 * | 1/1992 | Bond et al. ...................... 601/33 |
| 5,090,421 * | 2/1992 | Wagoner, III .................... 128/774 |
| 5,116,296 * | 5/1992 | Watkins et al. .................... 482/91 |
| 5,121,747 * | 6/1992 | Andrews ......................... 607/2 |

OTHER PUBLICATIONS

Gough, J. et al., An Investigation Into the Effectiveness of Various Forms of Quadriceps Exercises, Physiotherapy, 57(8), pp. 356–361 (1971).

Skurja, M., Quadriceps Action in Straight Leg Raise Versus Isolated Knee Extenstion (EMG and Tension Study), Physical Therapy, 60, 582 (1980).

Stratford, P., Electromyography of the Quadriceps Femoris Muscles in Subjects With Normal Knees and Acutely Effused Knees, Physical Therapy, vol. 62, No. 3, pp. 279–283 (1981).

Krebs, D. et al., Knee Joing Angle: Its Relationship to Quadriceps Femoris Activity in Normal and Post–arthrotomy Limbs, Arch. Phys. Med. Rehabil., vol. 64, pp. 441–447 (1983).

Soderberg, G. et al., Electromyographic Analysis of Knee Exercises in Healthy Subjects and in Patients With Knee Pathologies, Physical Therapy, vol. 67, No. 11, pp. 1691–1696 (1987).

Lindh, M., Increase of Muscle Strength From Isomeric Quadriceps Exercises at Different Knee Angles, Scand. J. Rehab. Med., 11, pp. 33–36 (1979).

Henry, F.M. et al., Relationships Between Individual Differences is Strength, Speed, and Mass in an Arm Movement, The Research Quarterly, vol. 31, No. 1, pp. 24–33 (1959).

Rasch, P., Progressive Resistance Exercise: Isotonic and Isometric: A Review, J.A.P.M.R., vol. 15, No. 2, pp. 46–50 (1961).

Wild, J. et al., Patellar Pain and Quadriceps Rehabilitation, An EMG Study, The American Journal of Sports Medicine, vol. 10, No. 1, pp. 12–15.

Antich, T.J. et al., Modification of Quadriceps Femoris Muscle Exercises During Knee Rehabilitation, Physical Therapy, vol. 66, No. 8, pp. 1246–1251 (1986).

Allington, R. et al., Strengthening Techniques of the Quadriceps Muscles: An Electromyographic Evaluation, Journal of the American Therapy Association, vol. 66, No. 11, pp. 1173–1176 (1966).

Haberichter, P.A. et al., Muscle Pressure Effects on Motorneuron Excitability, Physical Therapy, vol. 65, No. 5, p. 723 (1985).

Soderberg et al., An Electromyographic Analysis of Quadriceps Femoris Muscle Setting and Straight Leg Raising, vol. 63, No. 9, pp. 1434–1438.

\* cited by examiner

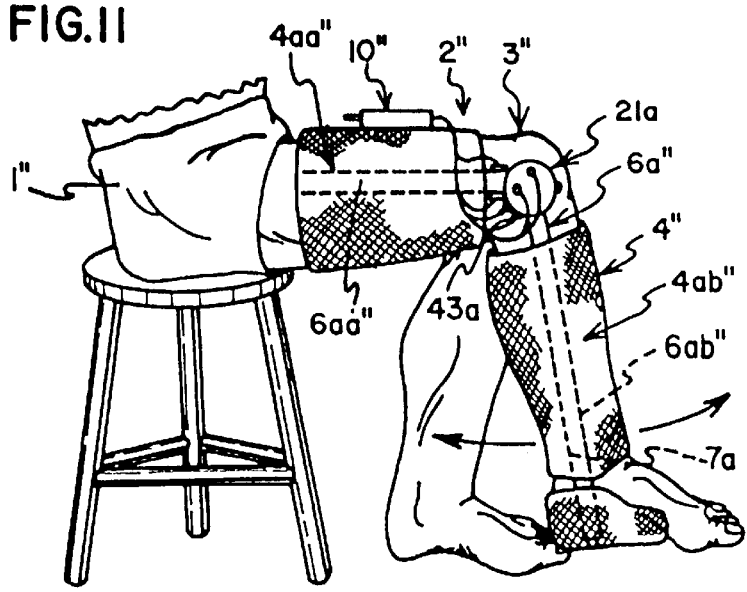
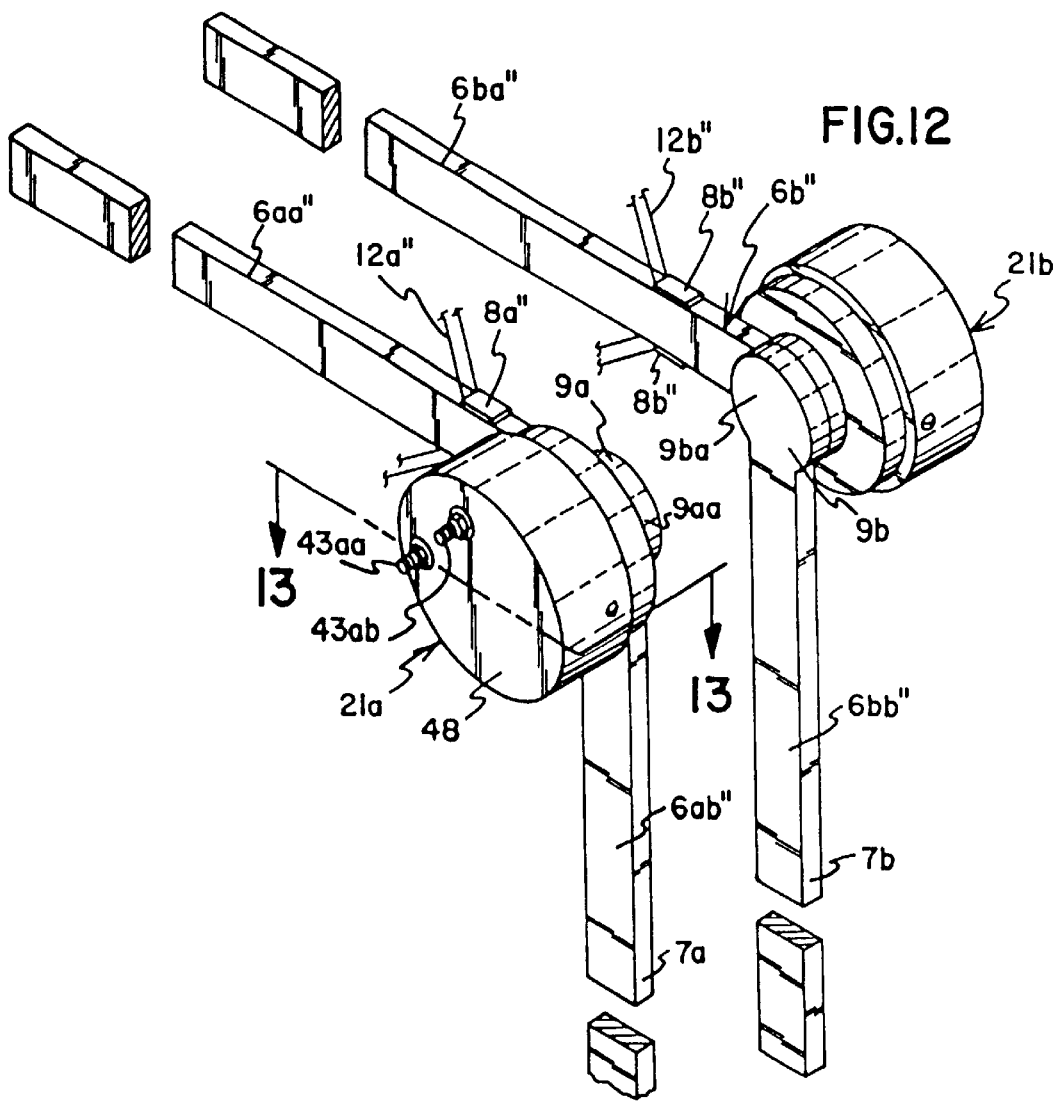

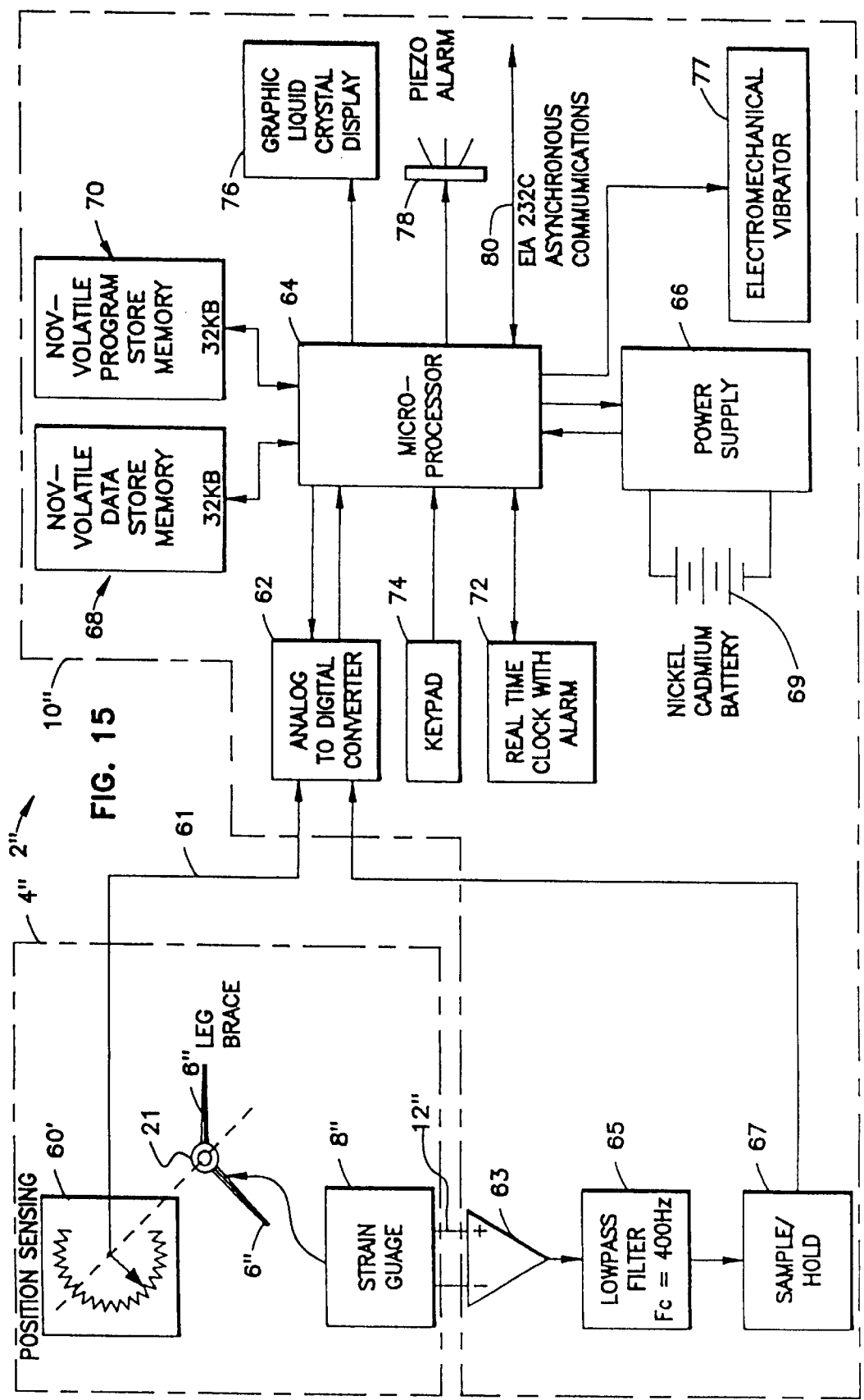

METHOD OF OPTIMIZING ISOMETRIC EXERCISE

This is a continuation of application Ser. No. 08/298,591, now U.S. Pat. 5,484,389, filed Aug. 31, 1994, which in turn is a Continuation of application Ser. No. 07/733,207, now U.S. Pat. No. 5,368,546, filed Jul. 19, 1991, which is a Continuation of application Ser. No. 07/483,139, now U.S. Pat. No. 5,052,375, filed on Feb. 21, 1990.

FIELD OF THE INVENTION

The present invention relates to ambulatory orthopedic restraining devices such as casts, braces and the like.

BACKGROUND OF THE INVENTION

It is known that both muscles and bones should be exercised to maintain strength. It is also known that healing fractures, exposed to permissible weight bearing stress, often heal more predictably and more rapidly than fractures which are not stressed at all. This is probably also true for connective tissues, such as ligaments and particular cartilage.

When an individual sustains a physical injury which involves damage to bones, muscle tissue, connective tissue or the like, the physician treating the individual will make a determination as to whether exercise will be allowed. The physician will allow exercise if the physician can obtain assurances that the exercise will be performed in a controlled manner within specific parameters wherein the injured bone and/or tissue will remain stable. Unfortunately, however, the physician is generally unable to obtain adequate information or assurances about the manner in which a particular patient will conduct prescribed exercise. Furthermore, because the physician is also unable to obtain adequate feedback after the patient performs any specific prescribed exercise, the physician generally does not feel he or she has sufficient access to information about the exercise to permit or recommend anything but the most basic exercise. Without some way to obtain information about exercise events, the physician cannot maintain sufficient control of the exercise. The physician does not know how much stress the patient can or will exert voluntarily, and does not know how well the patient will adhere to a schedule of repetitive exercise events.

Since the physician is not able to obtain adequate feedback regarding the patient's exercise, the most prudent course of action for the physician is to limit the amount of exercise which the patient is allowed to perform by immobilizing the portions of the body proximate the injury. This is often accomplished by using a cast which is the simplest and crudest method of protecting an injury. The cast allows virtually no movement at all and is widely used to insure against reinjuries. Unfortunately, this method of protecting the injury often does not provide adequate means for exercising the body portions proximate the injury. For instance, a cast is often not strong enough, without additional reinforcement, to permit isometric exercising. Furthermore, casts are not equipped to provide feedback to the physician or the patient with respect to any exercising.

Accordingly, a need exists for a personal orthopedic restraining device which will permit and encourage a range of exercise during rehabilitation and provide sufficient feedback to the prescribing physician to allow the physician to evaluate the patient's progress in regard to the exercise the physician has prescribed. A need also exists for a personal restraining device which is equipped to give the patient immediate feedback respecting exercise events. Although it has been known that exercise is helpful in rehabilitating patients and others having orthopedic disabilities, inadequacies, or the like, adequate devices for methods of restraining respective body parts and monitoring the exercise thereof have not been provided which adequately address this problem.

The present invention provides a solution to these and other problems, and offers other advantages over the prior art.

SUMMARY OF THE INVENTION

Accordingly, a novel orthopedic restraining device is now proposed. The present invention provides a personal orthopedic restraining device for use to restrain flexibly connected body portions of an individual. The present restraining device comprises an ambulatory housing, including first and second distal end portions, and restraining means for restraining movement of said first and second distal end portions relative to one another. Each of the respective distal end portions is configured to receive flexibly connected body portions of the individual, whereby movement of the respective body portions relative to one another can be restrained by the housing. The present restraining device also comprises stress sensing means for sensing stress on said restraining means and stress indicating means for indicating a quantitative stress value based upon an output from said stress sensing means. Said stress sensing means is attached to said restraining means and said stress indicating means is interconnected with said stress sensing means for receiving the output from said stress sensing means. In preferred embodiments, said restraining means include an elongated restraining bar having first and second distal end sections, wherein said first and second distal end sections are fixedly secured to said first and second distal end portions of the housing, respectively. In the most preferred devices, the restraining device is preferably an ambulatory appliance which can be worn by the individual to prevent specific movements of respective body portions restrained thereby. Certain stress placed upon said restraining means can be monitored with said indicating means. Preferably, the present restraining device further includes recording means for recording an output from said stress sensing means, wherein said recording means is interconnected with said stress sensing means for receiving the output from said stress sensing means. A preferred restraining device of the present invention further includes control means including said indicating means and said recording means and being interconnected with said stress sensing means for receiving the output from said stress sensing means. Preferably, said control means further include microprocessor means for processing outputs from said stress sensing means. The elongated restraining bar can include an adjustable hinge interconnecting said distal end sections, wherein the angular position of the respective distal end sections can be adjusted relative to one another. In preferred embodiments, the adjustable hinge includes position sensing means for sensing the relative angular position of the first and second distal end sections. In certain preferred embodiments, the adjustable hinge is an electromechanical hinge and the restraining device includes control means interconnected with said stress sensing means and said position sensing means for receiving outputs therefrom. Preferably, said control means further include recording means for recording outputs from said stress sensing means and said positioning sensing means. Said stress sensing means preferably include a strain gauge, more preferably a plurality of strain gauges, attached to said restraining means, preferably attached to the elongated restraining bar. In a preferred embodiment, stress sensing means include four strain gauges attached to the elongated restraining bar and being interconnected with one another in a wheatstone bridge circuit arrangement. Preferably, the present restraining device will have two elongated restraining bars disposed on opposite sides of the flexibly connected body portions when the housing is engaged therewith.

Alternate embodiments of the present invention provide methods of rehabilitating or conditioning an individual having orthopedic or musculoskeletal disabilities or deficits and of monitoring and regulating patient musculoskeletal rehabilitation and/or conditioning. Each of these methods preferably comprise the steps of providing a preferred restraining device of the present invention, engaging flexibly connected body portions in the device and exercising, or requesting the individual to exercise, the respective flexibly connected body portions by exerting a measurable force against said restraining means. Further steps including monitoring stress placed upon said restraining means. In preferred embodiments of the present method claims, the step of providing includes providing a preferred restraining device including an elongated restraining bar having an incrementally adjustable hinge interconnecting the first and second end sections, wherein the incrementally adjustable hinge permits the relative angular position of the first and second end sections to be adjusted incrementally such that the relative angular relationship of the respective body portions restrained thereby can be varied. When the adjustable hinge is used, physicians and physical therapists can direct a patient to adjust the hinge so that a series of sets of isometric exercises can be conducted at different degrees of flexion or extension, thereby allowing the patient to take advantage of the overlapping strength gains which are generally believed to be associated with isometric exercise events completed at any particular series of degrees of flexion.

Still other embodiments of the present invention include the step of providing a variety of other preferred embodiments of the restraining device of the present invention, including embodiments which incorporate a capacity for recording data generated by sensing means attached to an elongated restraining bar or bars. That data can be monitored by the patient and/or the physician or physical therapist during exercise and can also be stored and manipulated to allow the physician or physical therapist to monitor the patient's exercise at a later time and place, so that the patient's progress can be easily monitored and exercise behavior and response thereto. Control means (e.g., software) has also been developed to provide the patient with ideal exercise models or goals toward which the patient can strive. These models and/or goals can be used to enhance the patient's devotion to conditioning and/or rehabilitation, as well as to reinforce the patient's confidence in exercise generally and in the use of the preferred restraining device itself.

The present invention provides many advantages over the prior art methods of orthopedic immobilization. A more refined technique of immobilization is provided wherein the maximum strains exerted by a patient may be monitored, both by the patient and by the physician. Because the physician is able to obtain data regarding the patient's exercise ability and/or progress, the physician may permit the patient to exercise tissue surrounding an injury. The ability to retrieve information regarding such exercise gives the physician a degree of control over the exercise performed. For instance, after a review of the exercise conducted by the patient, the physician can prescribe more exercise when more exercise is believed to be appropriate, or less exercise when a patient is too aggressive. The physician can also advise and encourage the patient as to ways to modify the exercise routine so as to further benefit the patient and speed recovery or rehabilitation.

The injured body portions need only be immobilized as much as it is deemed to be required by the physician. As the physician obtains more information with respect to the exercise being conducted by the patient, the degree of immobilization and the exercise routine, can be varied to speed the patient's recovery and to suit a patient's immediate needs.

Significant cost savings may be realized with the availability of the present restraining device because frequent visits to the physical therapist for exercise therapy may no longer be required. Therapy programs for rehabilitation and/or conditioning following certain injuries can commonly cost the patient and society thousands of dollars. The present invention would provide a significant improvement over such therapy programs because the patient could exercise at home by following an exercise routine. The patient would be able to monitor his or her progress as would the physician when the preferred restraining device including recording means is used. It is envisioned that an exercise routine could be programmed directly into preferred embodiments of the present invention so that the patient could simply follow a preselected exercise routine at the same time that he or she monitors the effort being exerted. In other embodiments, it is envisioned that the patient's progress could be monitored locally or remotely by the physician or therapist entirely by electronic means, and that the exercise program could be varied in response to events, such as the completion of particular requirements.

Another significant advantage of the preferred embodiments of the present invention is that patient compliance is likely to be much higher. Because patients provided with preferred embodiments of the present invention will be able to monitor their own exercise routines, and will know, in certain cases, that their progress will be monitored by others, they are more likely to exercise as suggested by the physician. Forgetfulness could be obviated by a reminding device such as an alarm or a message system. Control means, preferably a computer program, can be provided which will provide a variable message system which can direct the patient's activity in either a set format or in a format which is responsive to the patient's success or failure with respect to specific goals or levels of exercise achievement. Patient confidence and devotion to rehabilitation efforts are also likely to be higher due to a knowledge that their efforts to rehabilitate their injury are being closely supervised. In addition, patient comfort level would undoubtedly be improved because of this increased confidence and devotion to rehabilitation, thereby lowering mental stresses which ordinarily result from fears that their injury is not being closely monitored or that progress with respect to rehabilitation is too subjective to identify. Furthermore, patients would probably have less pain due to unnecessary immobilization, and they would be able to retrieve hard data respecting their exercise routines which they could discuss objectively with their physician or physical therapist either in the office, or, in all likelihood, over the telephone subsequent to independent reviews of the data by each party.

The biggest advantage, however, is that patients will be able to recover from injuries quicker and will be able to avoid debilitating deterioration in strength of the tissue proximate the injury during periods of limited immobilization. The value of the present invention in this regard cannot be over emphasized. Physicians and therapists of the future will now have a means for obtaining feedback respecting patient exercise activity, which will permit them to allow constructive rehabilitative and maintenance conditioning which has, heretofore, been viewed as being too uncontrolled to be permitted in most cases.

It is also believed that patients will be able to perform exercise which they could not otherwise perform because of the availability of feedback when using preferred embodiments of the present invention. For instance, as a patient is able to achieve a certain level of exercise, they. will be reinforced with respect to their ability to perform the exercise. The exercise requirement can then be increased following the reinforcement, and the patient will then be given a further opportunity to obtain similar reinforcement with respect to reaching the next set of exercise requirements. Because the preferred embodiments of the present invention allow both the patient and the physician to monitor the patient's progress, the physician is more equipped to offer objective support and review of the patient's progress.

As used herein, an "isometric" exercise is an exercise wherein one exerts force against a restraining device having a set and substantially unchangeable configuration for the duration of the specific isometric exercise event. "Isometric" force means force which is exerted by pressing against a relatively immovable object, or two or more objects or elements of an apparatus or device which are relatively immovable with respect to one another. The incrementally adjustable hinge of an alternate embodiment of the present invention is designed to be adjustable between separate exercise events. As used herein, the phrase "angular position of the respective distal end sections" is used to describe an angular relationship or an angle or angles between the longitudinal axes of the respective first and second end sections of an elongated restraining bar or a pair of elongated restraining bars having reciprocating angular relationships between their respective distal end sections. Although it is envisioned that the primary emphasis for use of the present invention will be with human beings, particularly patients recovery a wide assortment of injuries or disabilities, as used herein an "individual" can be a human or an animal such as a horse, cat, dog, or any other domestic or wild animal. An "ambulatory" housing, or an "ambulatory" appliance, as used herein, is a housing or an appliance which may be engaged with flexibly connected body portions of an individual such that the individual can move from place to place wearing the housing or appliance which is so described. As used herein, "flexibly connected body portions" of an individual are flexibly connected body parts such as an upper leg and a lower leg which are flexibly interconnected at the knee, an upper arm and a forearm which are flexibly interconnected at the elbow, a forearm and a hand which are flexibly interconnected at the wrist, separate portions of one's torso which are flexibly interconnected at any one of the flexible joints between any two vertebra, and the like. Elements of the present invention which are "interconnected for receiving outputs" include elements which are interconnected electrically or are interconnected by means such that signals and/or information or outputs can be transmitted and received between said elements via a wired or wireless connection. As used herein in connection with the terms "indication" and "indicator", "audible" means an indication or indicator capable of being sensed using one's sense of hearing; "visual" means an indication or indicator capable of being sensed using one's ability to see; and "palpable" means an indication or indicator capable of being sensed using one's sense of feeling. The term "instrumented", as used herein, means "including mechanisms for monitoring outputs".

These and various other advantages and features of novelty which characterize the present invention are pointed out with particularity in the claims annexed hereto and forming a part hereof. However, for a better understanding of the invention, its advantages, and the objects obtained by its use, reference should be made to the drawings which form a further part hereof and to the accompanying descriptive material, in which there is illustrated and described preferred embodiments of the present invention.

In the drawings, in which like reference numerals refer to corresponding parts of preferred embodiments of the present invention throughout the several views, FIG. 1 is a side view of an orthopedic restraining device in accordance with the present invention;

FIG. 11 is a side view of an alternate orthopedic restraining device having an electromechanical hinge;

FIG. 12 is a schematic illustration of elements of the alternate orthopedic restraining device shown in FIG. 11;

FIG. 15 is a functional block diagram of the orthopedic restraining device shown in FIGS. 11–14.

DETAILED DESCRIPTION OF THE PREFERRED EMBODIMENTS

Figure 1:
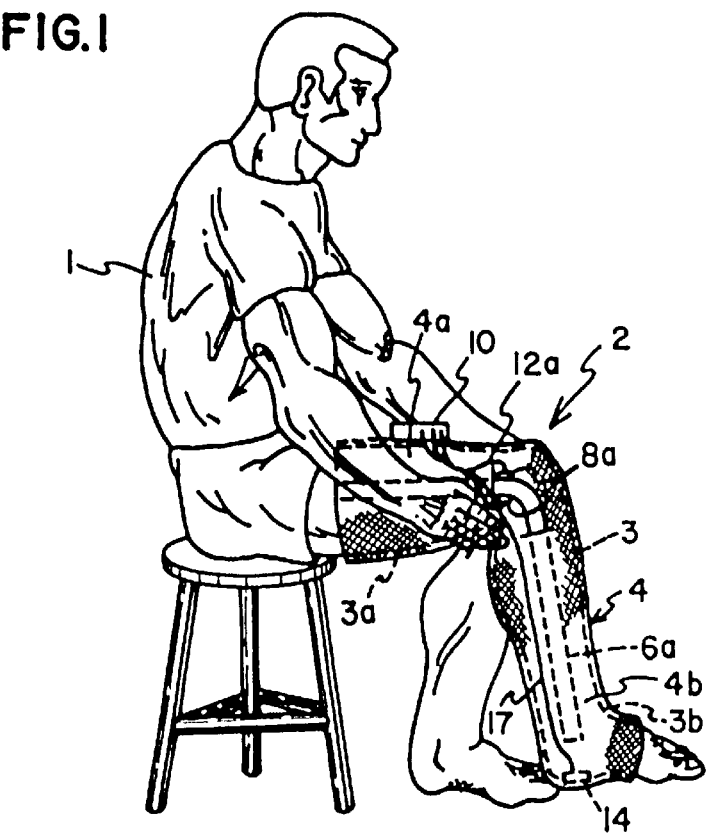

Prior to describing the prepared embodiments of the present inventions, the following background material is provided as a further foundation to support an understanding of the advantages the present invention offers over the prior art.

The process of strengthening the extremities is an essential element in orthopedic and rehabilitation treatment.

Many patients suffering from joint, ligament, or muscle damage or disease could function better if they had adequate motor power to control the damaged or diseased tissue. Strengthening the damaged or diseased extremity, when it can be achieved, is a safe and normally effective way of improving function. Therefore, treating physicians generally resort to strengthening quite early in the treatment process.

Strengthening is not always achieved, however. Failure to strengthen the extremity may occur because of poor patient understanding, lack of motivation or pain. It may also result because of the apparent contradiction between the need to protect the damaged or diseased tissue from further trauma and the need for exercise.

In order to provide for improved strengthening procedures, the orthopedic and physical therapy communities need an improved means to control the damaged or diseased extremity while:

1. Encouraging strengthening through feedback.
2. Controlling the strengthening by monitoring.
3. Storing the data for subsequent interpretation.

The present device attempts to do this.

Motivational psychology is often enough to prompt a patient to overcome pain when strengthening is necessary. It is, however, not always enough. We are all familiar with the highly motivated athlete who can overcome pain to rehabilitate himself or herself. Few of us think of the severely diseased elderly rheumatoid patient, however, who may be unable to bear any additional amount of pain in an attempt to overcome his or her disease. Psychology works in favor of the athlete because the athlete is a motivated individual. Psychology works against the elderly rheumatoid patient, however, because of depression, anxiety, and fear of pain. The effectiveness of a strengthening program must be measured by its ability to enable the patient to maximize the strengthening which is technically possible in each one of the aforementioned cases.

Strengthening can be optimized by utilizing the technological advances embodied in the present invention. If the exercise program fails for some reason, the data provided by the device will provide an indication of how the exercise program is failing. Patterns of response would indicate the pattern of failure, whether it is motivation, inhibition by pain, lack of commitment or submaximal effort (to name a few possible reasons for failure). The present device attempts to collect and provide objective feedback which can be analyzed by the patient and/or the prescribing physician or therapist. It is really a system. A system of controlling an injured extremity. It will motivate the individual and monitor his or her progress for safety and efficiency. It may also have significant applications for uninjured individuals as well.

The advantages of the present device over prior devices include:

1. Its sophistication.
2. Its complex relationship of several otherwise unrelated principles of physiology and engineering.
3. Its recording and documentation abilities.
4. Its ability to motivate and remind the individual.

Strengthening programs using isometric means have been demonstrated in the past to have important predictable affects on strengthening. However, the programs have generally been executed in isolation by the patient. The conventional physical therapy programs often work because of the intense coaching and supportive environment which the physical therapy setting provides. This involves extraordinary expenses, however, just to overcome motivational and psychological factors. Theoretically, many of the modalities provided in the therapist's office could be administered at home if the patient could obtain enough emotional support, control, and motivation by other means.

The present device will enhance the patient's ability to receive the support, control and motivation needed for an effective program of treatment. Because the device is fairly sophisticated, some formal training may be necessary for those prescribing its use. The potential need for the device, however, could be tremendous given frequency volume of orthopedic injury and disease.

The strengthening of muscle has become a science. There are many methods available, and among those methods, there are various proponents of specific techniques and various attitudes about timing, magnitude of stress, overall training periods and the like.

The isometric method which is the method primarily employed by present invention, has advantages and some disadvantages. It should not be suggested as a replacement for all other types of strengthening. Strengthening effects are often very specific to individual conditioning or individual body structure. Instead, the isometric method should be considered an adjunct or, in certain cases, the only possible method in light of the particular damage, disease or other changes.

There are basically three different methods for muscle strengthening. They are: first, isotonic, second, isokinetic, and, third, isometric.

Isotonic literally means same weight or same resistance. The best example of an isotonic exercise is the body builder with free weights. Basically when the body builder picks up a 100 pound weight, it weighs 100 pounds through the entire range of motion. It weighs 100 pounds regardless of whether or not the individual can generate 100 pounds of resistance to move it. If there is injury or pain, there is no way to relieve the body of that 100 pound weight. The muscle and body complex must, through injury or pain, either drop the weight risking further injury, or set it down under control, again risking further injury and pain.

How can a simple 100 pound free weight cause an individual to risk injury? The common individual has little difficulty exerting 100, 200 or more pounds of force in a squat or on certain types of resistive machines. An example of such a resistive machine is the so-called knee bench. An individual sitting on the bench is asked to extend the knee against resistance, usually that resistance is provided through a cable, sling or bracket which fits across the leg and is mechanically connected to the weight. Through an attempt at knee extension, the weight moves up and down against gravity. The problem with this type of device results when the knee becomes painful or cartilage damage results. If cartilage damage or pain results of 45° flexion, the patient must still relax the knee another 45° down to 90° of flexion before the weight and stresses are relieved. It is this movement under stress or pain which proponents of isokinetic knee exercise equipment have a great issue. It is one of the arguments used to advocate isokinetic exercise.

The term isokinetic literally means "same motion". The person exerting against an isokinetic machine exerts a maximal amount, whatever that amount is, and the machine provides only that identical amount of resistance. For example, if a delicate female, in pain, can only exert 10 pounds of resistance to straighten the knee, the attached machine will provide only 10 pounds of resistance. This is under the control of the professional administrating the treatment. Returning to the example of the football player, running down the field moves the knee at a specific angular rate which approximates 300° per second. (The knee is moving from flexion to extension and back). Isokinetic proponents argue that training should therefore occur at 300° per second and that the best possible training will occur if the patient is trained to exert his maximal force at a rate, not a fixed resistance.

This relates to the specificity philosophy of training. Specificity training means that training should most accurately reproduce that which will be exerted on the playing field.

These are valid arguments and are highly appropriate to he otherwise healthy knee requiring a maximum amount of strengthening. Isokinetic exercise does not interfere or compete with isometric exercise.

There are patients, however, who cannot exercise against an isokinetic machine, the knee hurts too much, the damaged surfaces are too painful, or the rapid motion of the knee against resistance under load results in further damage.

Isometric literally means "same length". The muscle is held at a fixed length and required to contract. This is the basis of the quadriceps setting exercise, the least stressful form of knee exercise and the exercise of last resort in the painful knee. A foundation of orthopedic treatment in the painful knee is to prescribe straight leg raising exercises. This is to avoid the risk of further damage and to avoid problems with equipment or transportation. One problem with isometric exercise is the muscle is exercised without motion and at one particular length, and the patient will probably derive a minimum amount of benefit for those dynamic activities of daily living requiring strength through a range of motion or at other muscle lengths. Examples of such activities include climbing stairs, running down a football field, stepping off a curb, and a variety of pivoting, twisting activities.

For those individuals where isokinetic exercise is inappropriate, the prescription of isometric exercise has included a variety of modifications, most of which are unsophisticated. We may ask each individual to lock one foot against the other and hold in it at a fixed degree while forcing the legs in opposition. This provides no control, no feedback, and no assurance that it is being done to a maximum extent. Also it is fairly laborious and boring.

We may ask the individual to plant his foot beneath a fixed object, such as a sofa or another chair, and ask him or her to attempt to lift the object without any form of fixation. The patient generally flexes or extends the joint, and the movement which results can cause further pain and damage, resulting in a failure of the exercise program.

We may ask the individual to report to the physical therapy department and use an isokinetic machine fixed at certain points of flexion. This gives a certain amount of readout, flexibility and feedback, but it is generally very expensive. It cannot generally be accomplished any more frequently than once or twice a day and must, because of time and expense, be self-limited. The patient must hopefully derive some personal benefit from this exercise method so that, when the time and expense dictate, it can be discontinued and the patient can go on to additional strengthening by other methods. After such a program, the patient may maintain some permanent benefits (which is unlikely) or deteriorate in function over time because of the limitations of availability. Often the ultimate result is that the patient is at the same level as before therapy started.

How can this data be interpreted and modified for the Patient's benefit? Knapik (1983) did an interesting study where he compared various forms of exercise including isometric exercise, isotonic exercise and isokinetic exercise. (Isokinetic exercises were done at various rates of movement). The information gained bears directly upon the problems outlined in this chapter. Knapik found the following:

1. Maximum torque is possible with isometric exercise.
2. Individuals vary in their torque curves (maximum torque over various degrees of flexion) and that these torque curves may be further modified by injury of disease.
3. "Isometric curves are valid reflections of isokinetic curves."
4. The individuals own torque curve should be studied as reflective of injury, disease, disability and the pattern of needed rehabilitation.
5. Isometric curves best represent the maximal voluntary capability of the muscle group.

There is a tremendous volume of literature data relating to the three basic types of muscle strengthening. The conclusions seem valid and applicable to the isometric conditioning device.

First of all, patients can generate their maximum torque with an isometric exercise. This is useful in that it suggests the patient's maximum ability to exercise is reflected by isometric exercise. For a patient who can barely generate any type of extension force, least of all against an isokinetic machine, the form of exercise which maximizes their abilities would be most useful.

The force curves through the range of motion do vary from individual to individual. This is a reflection of the patient's own mechanics, body make-up, muscle physiology and three dimensional joint anatomy. There are also a myriad of other factors. Knapik's paper suggests that the force curves should be measured and that isometric exercise is a valid way to measure them. The ambulatory personal orthopedic restraining device, or isometric conditioning device (ICD) of the present invention may, therefore, because of its portability, individuality and methods of reinforcement, be the best method of maximizing the rehabilitation program.

Because the isometric curve is an accurate reflection of the isokinetic curve, the use of isometric exercise has a direct and important applicability to the function of the diseased extremity. Knapik's study gives excellent credibility to isometric exercise under specific conditions. These conditions include varying the angle at which the exercise is performed.

In summary, isometric, isokinetic and isotonic exercise each have advantages and disadvantages. The strongest advantage associated with isometric exercise is that the injured or diseased extremity can be strengthened in the absence of motion, thereby preferably resulting in less pain and less tissue damage. With appropriate modifications, isometric exercises can be used to obtain results which begin to approximate the results generally obtained with isokinetic exercises in certain situations when isokinetic exercises are not possible. The fact that program modifications enable one to obtain some of the benefits of isokinetic exercise from isometric exercise is of critical importance to the usefulness of the present device.

The articulations of the human body, commonly called joints, are not simple structures. Each is a complex combination of mechanical alignment, and biophysical properties under the control of muscles which are of themselves, dynamic structures.

Joints are usually characterized in some simplistic fashion such as ball and socket, hinge, fixed, or the like. Ball and socket joints probably resemble the structures after which they are named, more than most other structures do. Hinge joints, on the other hand, vary greatly in their structure, mechanics and dynamic action, and possess only the more general characteristics of a simple hinge for which they are named.

Probably the "simplest" hinge joint would be the elbow. The two condyles of the elbow share nearly the same center of rotation. The condyles themselves are nearly circular when viewed laterally and the opposing surface, the olecranon (of the forearm, ulna), is nearly circular as well. This by itself simplifies the mechanics of joint understanding a great deal. Its simplicity, on the other hand, reflects the complexity of other joints, such as the knee.

Joints, being living structures, and being designed very specifically for appropriate measures of mechanical advantage, stress, weight distribution, rotational stability, and the like impose demands upon professionals who would seek to assist them to recover from injury and disease.

A hydraulic cylinder under pressure exhibits the same pressure near the end of its excursion as it does at its beginning. This is because the cylinder is uniform. The piston is unchanging. The mechanical effect of the hydraulic fluid is defined by that piston size, and as long as it is uniform, the mechanical effect is the same.

The muscle on the other hand is quite different. Muscle cannot extend an infinite distance. It works efficiently within a fairly narrow range between 0.7 and 1.2 times its resting length. It rapidly loses efficiency at either extreme. It's greatest efficiency is at a slight degree of lengthening beyond its resting length.

If one combines what is known about the elbow, arguably the simplest of the hinge joints, with the complexity of physiologic muscle which changes its efficiency over distance, one begins to understand the complexity of what is a simple joint/muscle construct.

If one now combines the complexity of muscle efficiency with a very complex joint, such as the knee, further complexities result. The knee is not a simple hinge joint, but is actually a cam working against a fairly flat surface. As the knee goes into flexion, the degree of excursion of the tendon increases. The pulley, across which the quadriceps tendon works, is not a simple round mechanical device, which is entirely uniform, but it is a rocking, pivoting, sliding structure, which is thicker in some areas than in others, and which exerts pressure through a greater surface area in some degrees of motion than in others. The patella is articulating with a cam-like surface, which is at a different point of flexion and relative prominence than the tibia, which is bearing against the femur in a different area. Finally, there is an element of rotation, because the two cam-like surfaces of the knee are not identically shaped. One is smaller, shorter and rounder than the other, causing the knee to "rotate out of the way" in flexion.

In effect then, what we have here are variables working upon variables. The muscle may be gaining efficiently because it is being stretched from its resting length but the mechanical advantage of its tendon may be gained or lost because of patellofemoral anatomy, rotation of the tibia or other change of normal joint physiology.

If one further compounds abnormal joint physiology with the inhibitory effects of a pain reflex, apprehension or poor cooperation, the problem can be fully appreciated.

The present invention provides a device which can be used to address the difficulties inherent in this set of variables. Because it is basically, a measuring, monitoring, and controlling device, the present device can, with proper use, minimize pain, control the extremity and measure output, strength, and cooperation.

The present device would be able to measure the individual strength curve for that particular subject and individual. The strength curve would likely fit, or fail to fit, a pattern as defined by research in the field. The interplay between the relative factors of muscle length and joint anatomy would be removed as they currently complicate isotonic and isokinetic types of exercise.

Removal of translational forces. If an individual has disruption of the joint surface, the normal translation of one surface over the other is disrupted. Such surfaces commonly can handle compressive loads fairly well, but the increased abrasion which occurs with translation of disrupted surfaces may further damage those symptoms or at a minimum aggravate the patient's symptoms. The discomfort which results from such translation through a spinal reflex may cause interference with the patient's voluntary attempts at exercise. It may cause involuntary interference as well. Finally, in a patient with emotional factors of anxiety or failure of understanding, the interplay between the volitional, involuntary, psychologic factors becomes a morass which obscures the process of strengthening.

In summary, some patients simply must have every possible advantage in order to benefit from a strengthening program. Some patients have the normal psychological make-up, strong need to recover and virtually any type of exercise program (or perhaps no exercise program at all) will be satisfactory to their needs. To those patients where such positive factors are not present, the negative factors must be addressed one by one, individually removing physiologic blocks to recovery. (such as reflex inhibition), anatomic blocks to recovery (such as joint irregularity), pain (such as might be experienced with attempts to move a recently operated joint), or failure of understanding (which with a sophisticated device, could not only instruct, but also record and reinforce for the patient).

At the current time, orthopedists as prescribing professionals for individuals with knee problems, often recommend straight leg raising exercises and quadriceps setting exercises for patients. The recommendation is often fairly nonspecific and based upon what the physician interprets the convenience of the patient to be. Quadriceps setting exercises are ordinarily performed with the patient sitting, the knee is usually fully extended and the patient is asked to forcefully contract their muscle, attempting to straighten it further. This ordinarily is demonstrated by some movement of the patella and a highlighting of the outline of the quadriceps and other muscles of the thigh. Straight leg raising exercises are usually performed with the patient supine on the floor. The patient is asked to raise his leg straight up, approximately 12 inches and allow it to rest again. Both exercises are done repetitively. The rationale behind these exercises is that they require the muscles to contract under minimal restriction, in a protected position (full extension) and since this requires no motion, it is generally accepted as being nonstressful and comfortable. Little has been recognized about the relative merits of these two different types of exercise as they apply to the specific muscles which require strengthening.

Gough and Ladley (1971, Physiotherapy 57:356–361) noticed that quadriceps contraction was greater with isometric exercises (quadriceps setting) than straight leg raising exercises.

Skuja et al. (1980, Physical Therapy 60:582) noted more activity in the vasti with isometric exercises as opposed to straight leg raising. Soderberg and Cook (1983 Physical Therapy 63:1434–1438), noted that only the rectus femoris was more active in straight leg raising exercises than during quadriceps setting exercises (isometric exercises) than with straight leg raising.

Stratford (1982, Physical Therapy 62:279–283) noticed decreased electromyographic activity at 0# in knees with effusions than at 30#, suggesting that slight tension of the muscles is important in the injured knee. Krebs et al. (1983) suggested highly significant position dependent effects of exercise in healthy and postarthrotomy knees.

Soderberg and Minor (1987) seem to confirm the conclusions of Soderberg and Cook (1983) when they demonstrated that quadriceps setting exercises increased activity in the vastus medialis, the biceps, and the gluteus medias. Straight leg raising exercises seemed to selectively result in more contraction of the rectus femoris muscle in a great majority of patients.

Haberichter et al. (1985, Physical Therapy 65:723) noted that slight pressure on the muscles seemed to have an effect on increased contractual force.

The summary of the above referenced articles suggests that: (A) quadriceps setting exercises are a separate and distinct type of exercise from straight leg raising exercises and have important effects on the majority of muscles about the knee (the vasti, the biceps and the gluteus); (B) that there is a position dependent effect of exercise in the injured knee; and (C) that modifications in patient's exercise program should be aimed specifically at maximizing the known effects of these two different types of exercise by: (1) applying slight tension and performing the exercises in flexion; (2) applying slight compression to the muscle; and/or (3) performing both straight leg raising exercises and isometric exercises.

These findings highlight the importance of control as it applies to an otherwise rather simple exercise without a restraining device. The quadriceps setting isometric exercise is extremely difficult to perform in a position other than full extension. The literature suggests that a change in position is important in the injured knee with effusion. Other literature suggests that multiple positions are important for maximal strengthening in knees with other types of problems.

This literature, particularly the article by Stratford, has led the applicants to believe that casts should be applied with the knee in slight flexion for physiological reasons. It is further suggested that contraction of the quadriceps muscle inside the cast may serve an important need at that fixed degree of flexion. A monitoring and controlling device, such as the present instrumented cast or brace, would therefore be very helpful.

Other inferences are also suggested by the literature. Most important among these is the inference that isometric exercise is separate and distinct from the straight leg raising exercise. In the applicants' opinion, it is difficult to instruct a patient in isometric quadriceps setting contraction because the patient will see no movement. Instructions to the patient to observe the knee cap or observe the contour of the quadriceps muscle are often met with a lack of understanding. This response often leaves the physician with questions as to: (A) whether or not the exercises will be performed (without a firm conviction of their significance, method and importance); and (B) if they are performed in the best possible manner, whether a monitoring and control device should be used to assist the patient to do this.

If the patient derives benefit from a straight leg raising exercise as an isolated exercise, which benefits the rectus femoris, then there is no reason why they could not do this exercise with an embodiment of the present device in place, thereby deriving the benefit of whatever weight and resistance the device could provide. The preferred embodiment of the present invention is obviously not intended for isolated strengthening of the rectus femoris if in fact, the rectus femoris is most well strengthened by straight leg raising.

However, questions are raised by the literature. These exercises, because of the limitations of prior art equipment, are all performed with the knee in extension or near full extension. It may be that once the knee is flexed, the straight leg raising exercise is no longer the best possible exercise for the rectus femoris. In addition, nothing is said about the wave form of the muscle contractions in any of these exercises. There is essentially no control over this aspect of the degree of isometric contraction. It would seem that slight contractions gradually building to a maximum crescendo, and then tapering off under voluntary control, may be a more elegant and more effective to perform isometric contractions.

Since the biceps (which is an antagonist of the quadriceps muscle) and the gluteus (which is related only peripherally and proximally) both demonstrate EMG activity other questions arise.

For instance, what is the effect on these muscles at various points of flexion. Something about the patient's. individual coordination may cause these muscles to fire as agonists or antagonists at various other points of flexion of the knee. Obtaining the definition of these effects is yet another advantage of the present invention. Muscles other than those obviously contracting and those obviously being protected by the device are being recruited. This suggests that the patient is getting a more general form of strengthening and conditioning by doing an isometric exercise. Therefore, anything which could encourage and monitor the isometric exercise program would benefit the patient more generally by affecting many muscles. In view of the foregoing, it will be appreciated that the advantages of isometric exercises will be enhanced through the use of the present invention.

In the next section, "Angular Specificity" is discussed. "Angular specificity" means the following: strength gains obtained with exercise, usually isometric exercise at one point of flexion, are associated with strength gains at adjacent points of flexion. Usually strength gains at those adjacent points of flexion are proportional to their proximity to the isolated point of flexion where the exercises are performed.

For example, if one does isometric exercise at 50 degrees of knee flexion, and one attempts to extend the knee beyond this point against infinite resistance, strength gains will be measurable at that point of flexion over time. In other words, the patient will be able to exert a greater force after regular exercise in 2 to 4 weeks. These strength gains will continue to increase within physiological limits as time passes. What is suggested in the literature is that similar strength gains will be measurable at points of flexion surrounding that 60 degree point so that the patient will be stronger also at 55 degrees, at 50 degrees, at 40 degrees. Literature data leads us to believe that this effect is measurable and fairly reliable in relatively small groups of study at points within 20 degrees of the point of maximal exercise. Some authors have suggested strength improvements well beyond that angle of exercise. Some have suggested strength improvements at 45 degrees from the angle of exercise. These strength improvements are more difficult to demonstrate, because a higher number of test subjects seem to be required. Statistics, individual variations, joint anatomy, and other factors come into play (Moffroid, Knapik, Lindh). Knapik (1983) exercised two groups of individuals; one by isometric means at 90 degrees of flexion, the other by isokinetic means between 45 and 135 degrees of flexion. He then measured both groups isometrically. He found out that isometrically gained strength at 70 degrees and 110 degrees was measurable and statistically comparable with the gain obtained at 90 degrees. He concluded that there was transfer of strength gain (angular specificity) within 20 degrees at the angle of the original exercise. Other literature suggests similar findings, that angular specificity is present, and that angular specificity, if overlapping, because of multiple points of exercise, may help the patient regain strength through the entire range of movement. It will be appreciated, therefore, that the isometric exercise routines of the present invention will greatly enhance the overall strength gains of the patient utilizing a device of the present invention.

Figure 2:
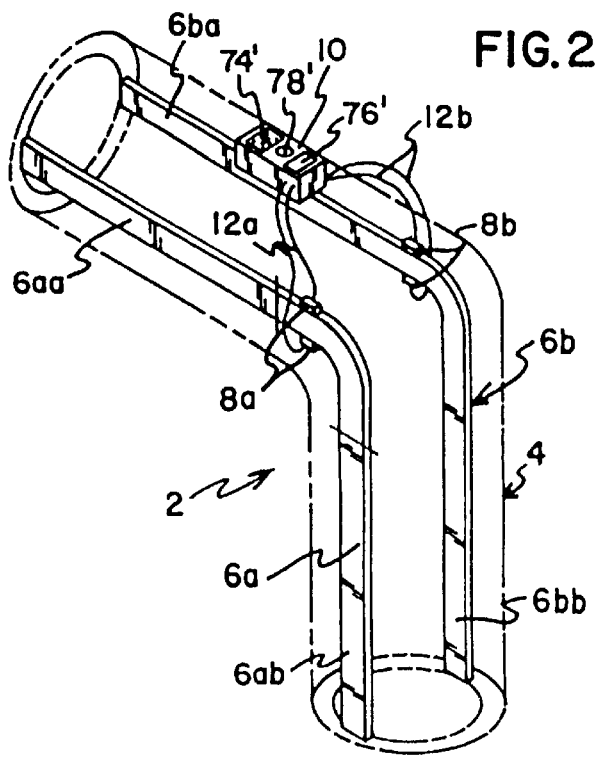
FIG. 2 is a schematic illustration of the orthopedic restraining device shown in FIG. 1 showing elongated restraining bars located on either side of the device.

Referring now to the drawings, and to FIGS. 1–2 in particular, a personal orthopedic restraining device 2 in accordance with the present invention is illustrated when engaged with upper and lower leg portions of a right leg 3 of an individual 1. The restraining device 2 includes a housing 4. The housing includes first and second distal end portions 4a and 4b which are configured to receive upper and lower leg portions 3a and 3b of the individual's right leg 3 which are flexibly connected at the knee. The housing 4 further includes a pair of elongated restraining bars 6a and 6b disposed on opposite sides of the individuals right leg 3. Each of the elongated restraining bars 6a and 6b have first and second distal end sections 6aa and 6ba, and 6ab and 6bb, respectively. Each of the distal end sections is fixedly secured to the respective end portion of the housing proximate thereto. Attached to opposite edges of each of the elongated restraining bars 6a and 6b are separate strain gauges 8a and 8b respectively. In preferred embodiments the strain gauges 8a and 8b are foil type strain gauges, each consisting of two strain gauges such that each elongated bar member 6a and 6b are equipped with four strain gauges which are interconnected in a wheatstone bridge circuit arrangement to provide superior sensing capabilities. The strain gauges are capable of sensing stress on the elongated restraining bars and provide an output which is indicative of a quantitative stress level. The strain gauges 8 are electrically interconnected with a programmed microprocessor control unit 10 which includes a mechanism for indicating a quantitative stress value based upon an output from the strain gauges 8 which sense stress on the respective elongated bar members 6a and 6b to which the individual strain gauges are attached. The device 2 also includes a pressure sensing mechanism or load cell 14 which senses pressure placed on the cell 14 when the individual places weight on the leg 3. The load cell 14 is interconnected by a wire 17 with the control unit 10 which can monitor and record outputs from the load cell 14.

An isometric restraining device 2 in accordance with the present invention includes a restraining mechanism 4 including an elongated restraining bar 6a, two strain gauges 8a attached to the restraining bar 6a, and a control unit 10, including a stress indicating mechanism, interconnected to the strain gauges 8a by interconnecting wires 12a. The restraining device 2 also includes a second elongated restraining bar 6b proximate the inside of the subject's leg such that it roughly mirrors the image of the restraining bar 6a which is shown on the outside of the subject's leg in FIG. 1. The other restraining bar 6b is also equipped with two strain gauges 8b which are attached to the bar and electrically interconnected to the control unit 10 in a similar manner to that shown in FIG. 1. Both restraining bars 6a and 6b are shown in FIG. 2.

Figure 3:
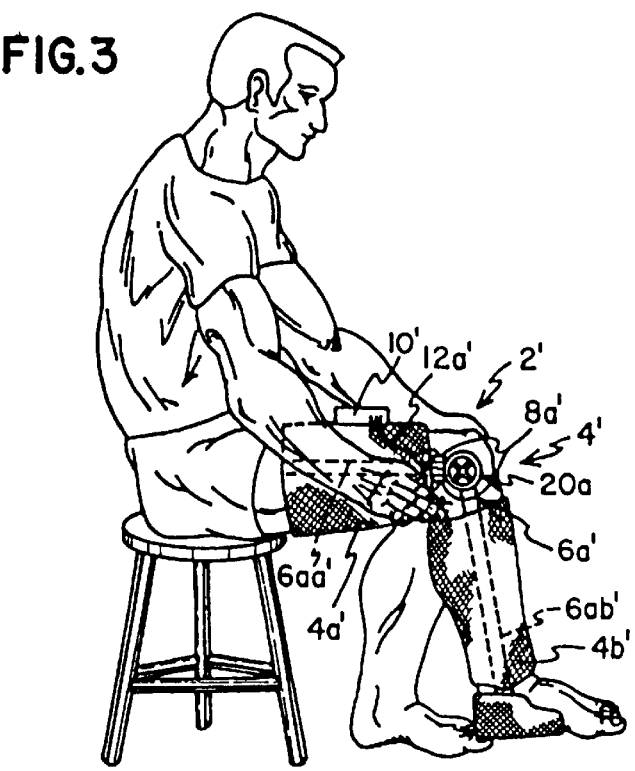
FIG. 3 is a side view of an alternate orthopedic restraining device in accordance with the present invention.
Figure 4:
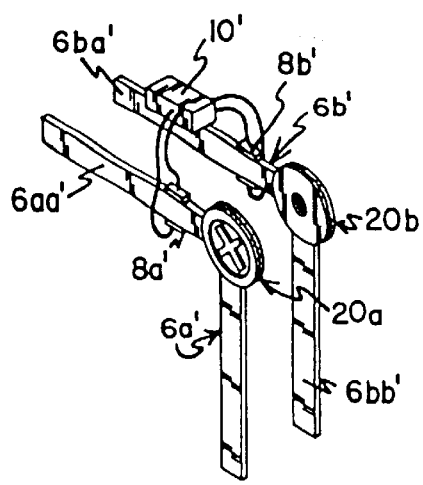
FIG. 4 is a schematic illustration of elements of the alternate orthopedic restraining device of FIG. 3 showing elongated restraining bars located on either side of the device.
Figure 5:
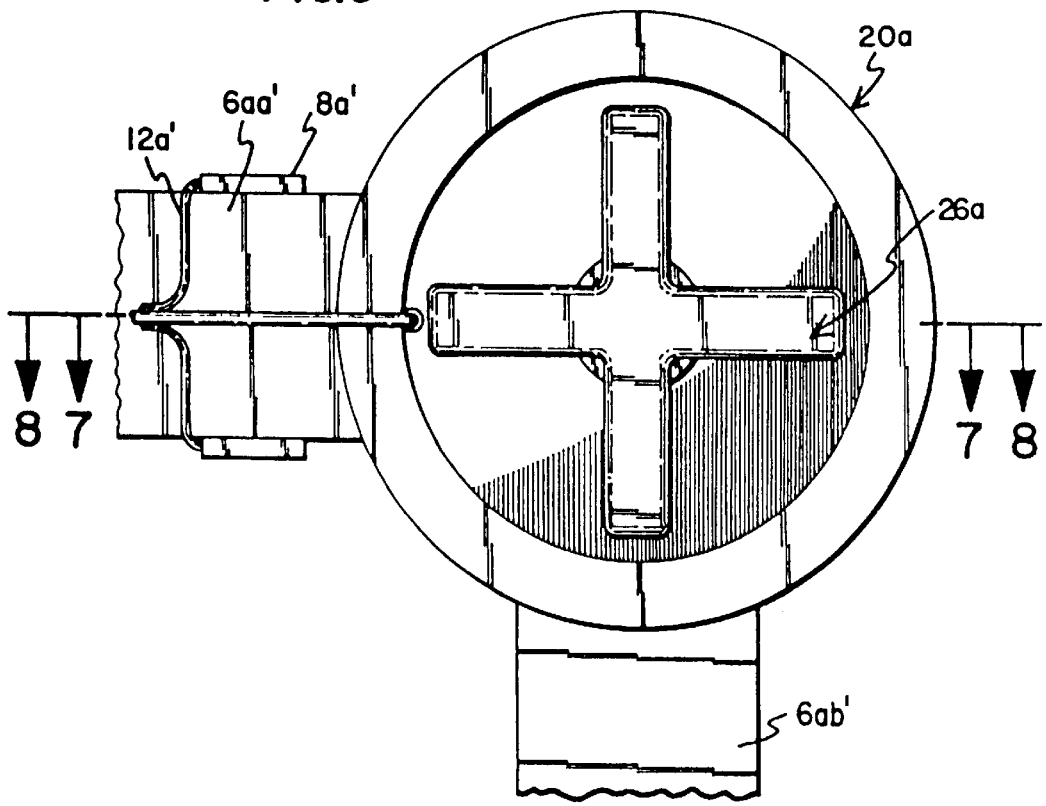
FIG. 5 is an enlarged side view of an incrementally adjustable hinge shown in FIG. 3.

Now referring also to FIGS. 3 and 4, the present invention also provides an alternate personal orthopedic restraining device 2' including elements corresponding to those of the previously described restraining device 2. In addition, however, each of the elongated restraining bars 6a' and 6b' include an incrementally adjustable hinge 20a or 20b interconnecting the respective distal end sections 6aa' and 6ab' or 6ba' and 6bb'. The first and second distal end portions 4a' and 4b' of the housing 4' are interconnected by the elongated restraining bars 6a' and 6b' which are fixedly secured thereto. The respective first distal end sections 6aa' and 6ba' are fixedly secured to the first distal end portion 4a' and the second distal end sections 6ab' and 6bb' (not shown) are fixedly secured to the second distal end portion 4b' so that these elements of the alternate restraining device 2' move as though they were separate portions of an integral unit. The plurality of strain gauges 8a' and 8b', respectively, are attached to the elongated restraining bars 6a' and 6b'. These strain gauges 8a' and 8b' are electrically interconnected with a control unit 10'.

It will be appreciated that the present invention may be made with a single strain gauge attached to a single elongated bar. However, it is preferable to include an elongated bar on either side of a point of flexion such as a knee, an elbow or the like. Similarly, it is preferable to include at least two strain gauges 8 on each of the elongated bars 6 and, preferably, four strain gauges in an unbalanced wheatstone bridge circuit arrangement or configuration.

Figure 6:
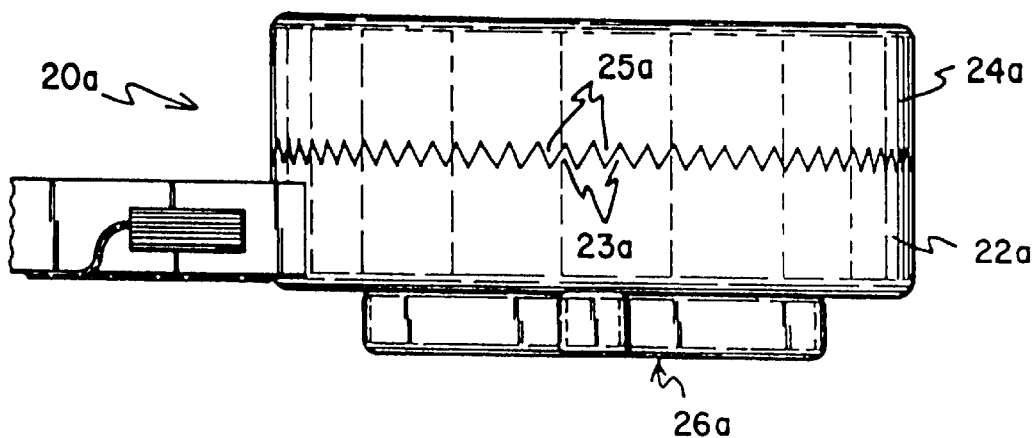
FIG. 6 is a top view of the adjustable hinge shown in FIG. 3 when its respective engaging members are engaged.
Figure 7:
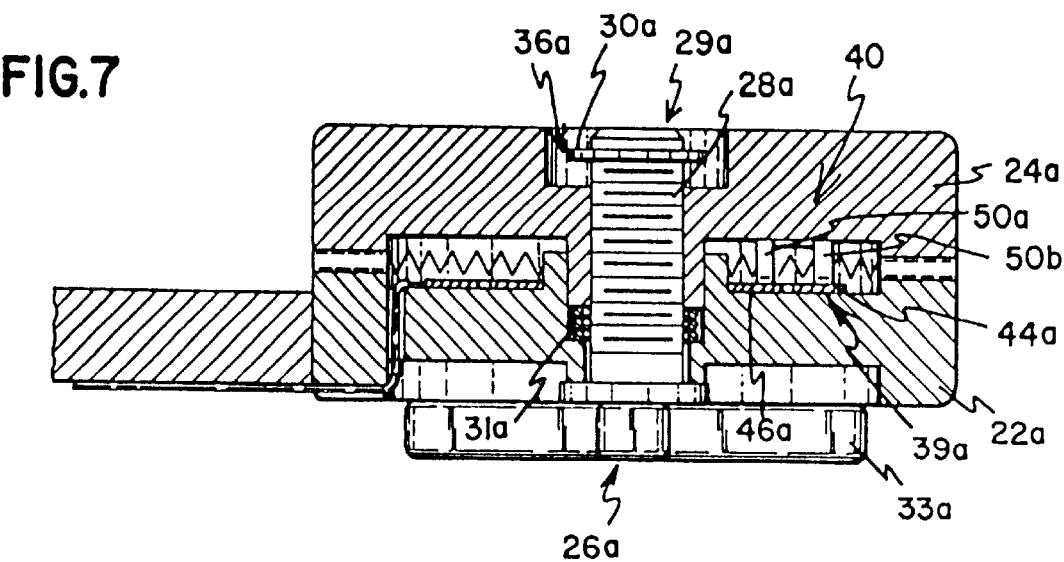
FIG. 7 is a sectional view of the adjustable hinge from the line 7—7 of FIG. 5 when the respective engaging members are engaged.
Figure 8:
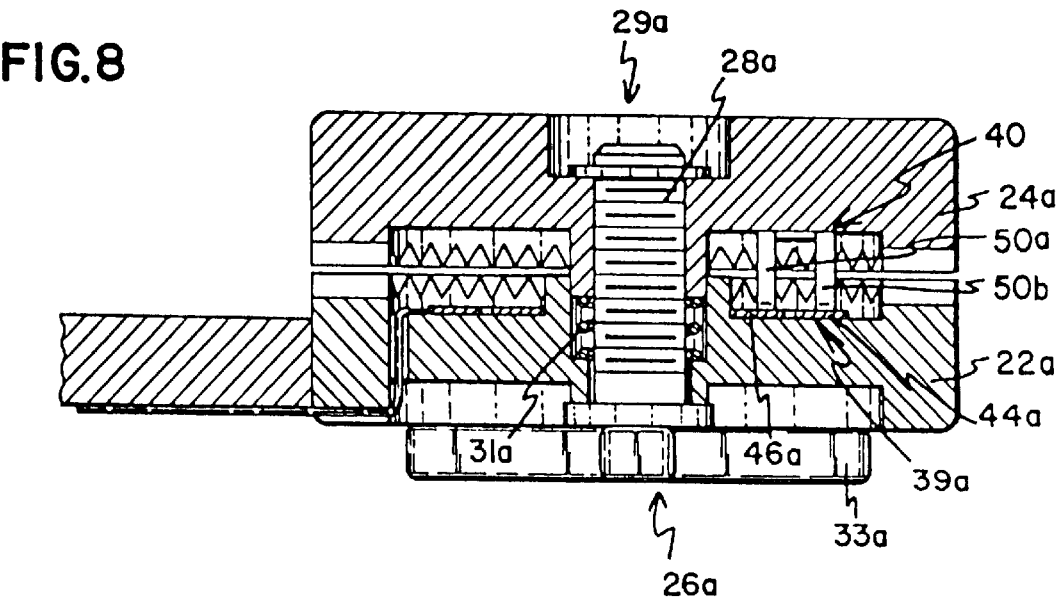
FIG. 8 is a sectional view of the adjustable hinge from line 8—8 of FIG. 5 when the respective engaging members are disengaged.

Referring now also to FIGS. 5–10, the adjustable hinge apparatus 20a includes a first engaging member 22a which is engagable with a second engaging member 24a. The first engaging member 22a is interconnected with the first distal end section 6aa of the elongated restraining bar 6a and the second engaging member 24a is interconnected with the second distal end section 6ab of the elongated restraining bar 6a. Each of the respective engaging members include engaging teeth, 23a and 25a respectively, which engage one another in a reciprocal relationship when the respective engaging members 22a and 24a are tightened or screwed together as shown in FIGS. 6 and 7. When the respective engaging members 22a and 24a are not tightened together, as shown in FIG. 8, they are free to turn or pivot with respect to one another on a bolt portion 28a of a securing member 26a which is retained within a bolt receiving opening 29a in the second engaging member 24a. The bolt receiving opening 29a is located in the circumferential center of the second engaging member 24a so that the bolt portion 28a of the securing member 26a provides an axial pivot point for the respective engaging members 22a and 24a, with respect to one another, when they are not secured together.

The bolt portion 28a of the securing member 26a is retained in the bolt receiving opening 29a by a retaining clip 30a which is attached to the bolt portion 28a such that the bolt portion 28a cannot be removed from the bolt receiving opening 29a. This prevents the securing member 26a from becoming entirely disengaged from the second engaging member 24a when the securing member 26a is unscrewed to free the engaging teeth 23a of the first engaging member 22a from the engaging teeth 25a of the second engaging member 24a. When the securing member 26a is unscrewed as far as the retaining clip 30a will allow the bolt portion 28a to go a coil spring 31a encircling the bolt portion 28a will bias the first engaging member 22a away from the second engaging member 24a so that the respective engaging teeth 23a and 25a are disengaged and the respective engaging members 22a and 24a can turn or pivot about the bolt portion 28a of the securing member 26a.

The bolt receiving opening 29a of the second engaging member 24a includes a reciprocating screw hole 34a which receives and reciprocates the right-handed screw turns on the bolt portion 28a of the securing member 26a. The bolt receiving opening 29a also includes a recess 36a. When the securing member 26a is turned clockwise, the right-handed screw turns of the bolt portion 28a are drawn into the second engaging member 24a by the reciprocating turns of the reciprocating screw hole 34a, and the respective engaging teeth 23a and 25a are gradually drawn closer together. When the securing member 26a is turned as far as it can go in this direction, the coil spring 31a will be tightened together as shown in FIG. 7, and the respective engaging teeth 23a and 25a will be tightened together and engaged such that the respective engaging members 22a and 24a can no longer turn or pivot with respect to one another.

When the engaging members 22a and 24a are tightened together in this manner, as shown in FIGS. 6 and 7, an angle between the respective distal end sections 6aa' and 6ab' of the elongated restraining bar 6a' will be fixed and the device 2' can then be used to restrain an individual wearing or engaged in the device 2' conducting isometric exercises at a series of different degree of flexion generally corresponding to this angle. This device 2' can also be used to restrain an individual conducting isometric exercises at a series of different degrees of flexion. This can be accomplished by conducting isometric exercises at one degree of flexion when the respective distal end sections 6aa' and 6ab' are set at one particular angle with respect to one another, and subsequently at a second, third, fourth and/or fifth degree of flexion when the respective distal end sections 6aa' and 6ab' are reset at different angles. It will be understood that this will mean resetting the angle between the respective end sections of each of the restraining bars 6a' and 6b' in a preferred device 2' which has two restraining bars. This is done by loosening the respective securing members 26a and 26b (not shown) on each side of the device 2', allowing the individual to adjust the flexion of the joint manually, and resecuring the respective engaging members 22a and 24 and 22b and 24b of the respective adjustable hinge apparatus 20a and 20b, such that the respective engaging teeth 23a and 25a and 23a and 25a of both of the adjustable hinges 20a and 20b are fully engaged as shown in FIGS. 6 and 7. When the engaging teeth are fully engaged, and the respective engaging members can no longer pivot with respect to one another, the angle between the respective distal end sections will be fixed and the subsequent isometric exercising can begin.

Preferred embodiments of the present invention also include a control unit 10. The control unit is interconnected with the respective strain gauges and the incrementally adjustable hinges in order that the control unit 10 can receive electrical outputs therefrom. The incrementally adjustable hinge 20a preferably includes a potentiometer-like mechanism 39a which is part of a position sensing device 60 for determining the angle of the respective distal end sections of the respective elongated restraining bar 6 in respect to one another. It will be appreciated that because the angle between respective end sections of respective restraining bars will generally be roughly equivalent, it is not required to have more than one potentiometer mechanism in any device 2'. However, because the elongated restraining bars 6a and 6b of the present device 2' are identical mirror images of one another, each includes the adjustable hinge apparatus 20a and 20b, respectively, including a potentiometer mechanism 39 which is interconnected with the control unit 10'. Each potentiometer mechanism has the same elements. Further embodiments of the hinge mechanism may include modification to better approximate the specific anatomic motion of the respective joint partially immobilized or protected by the specific device.

Figure 9:
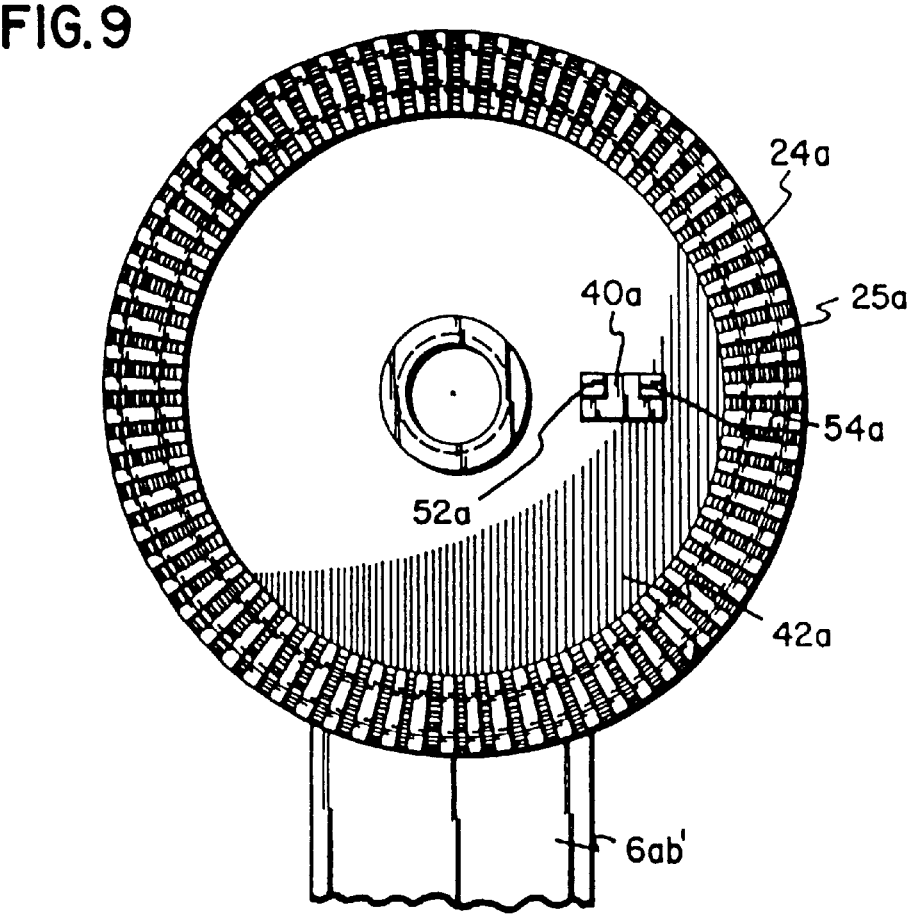
FIG. 9 is a side plan view of a first engaging member of the adjustable hinge shown in FIG. 6.
Figure 10:
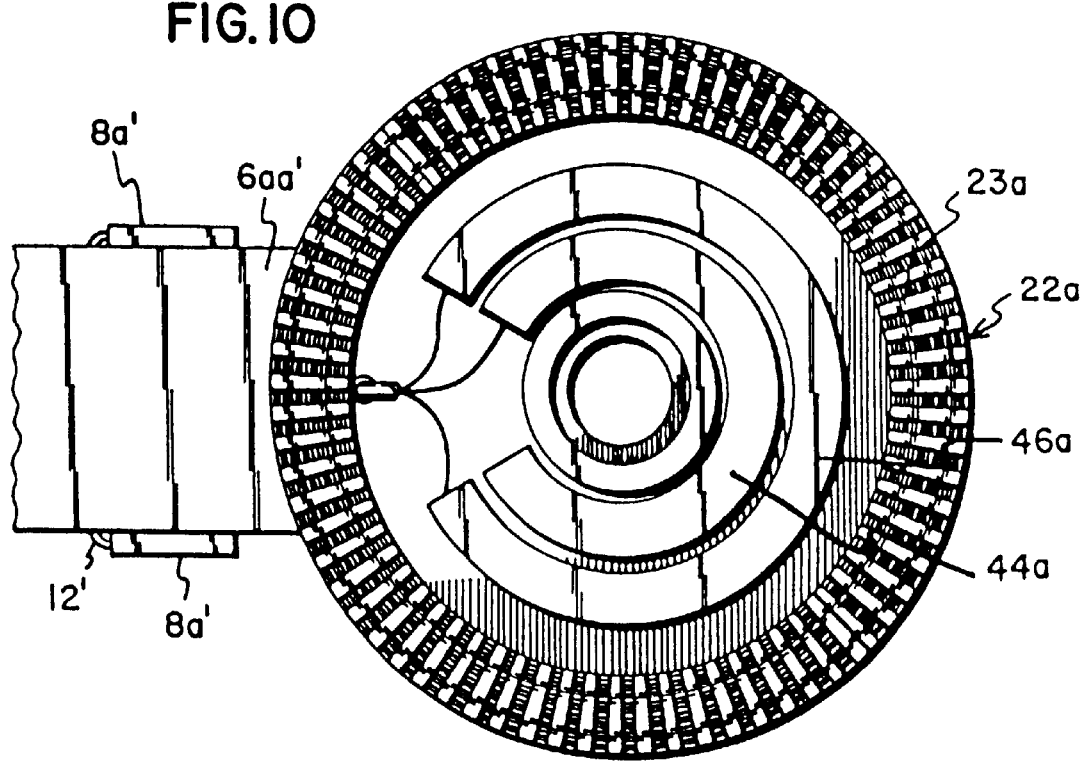
FIG. 10 is a side plan view of a second engaging member of the adjustable hinge shown in FIG. 6.

The potentiometer mechanism 39a shown in FIGS. 7 and 8 includes a conductive wiper 40a attached or adhered to an inner surface 42a of the second engaging member 24a, a resistive element 44a and a conductive element 46a which are interconnected with the control unit 10' in order that outputs from the potentiometer mechanism 39 can be monitored, and preferably, recorded, by the control unit 10' (See FIGS. 9 and 10 also). The wiper 40a has two resilient contact arms 52a and 54a which extend outwardly from the inner surface 42a of the second engaging member, 24a to contact the resistive element 44a and the conductive-element 46a, respectively, so that the position of the wiper 40a with respect to the resistive element 44a can be sensed by the control unit 10' reading the electrical output from the potentiometer mechanism 39. In embodiments where there are two hinges only one of the potentiometer mechanisms, if there are two, needs to be interconnected with the control unit 10', although both can be connected.

Figure 13:
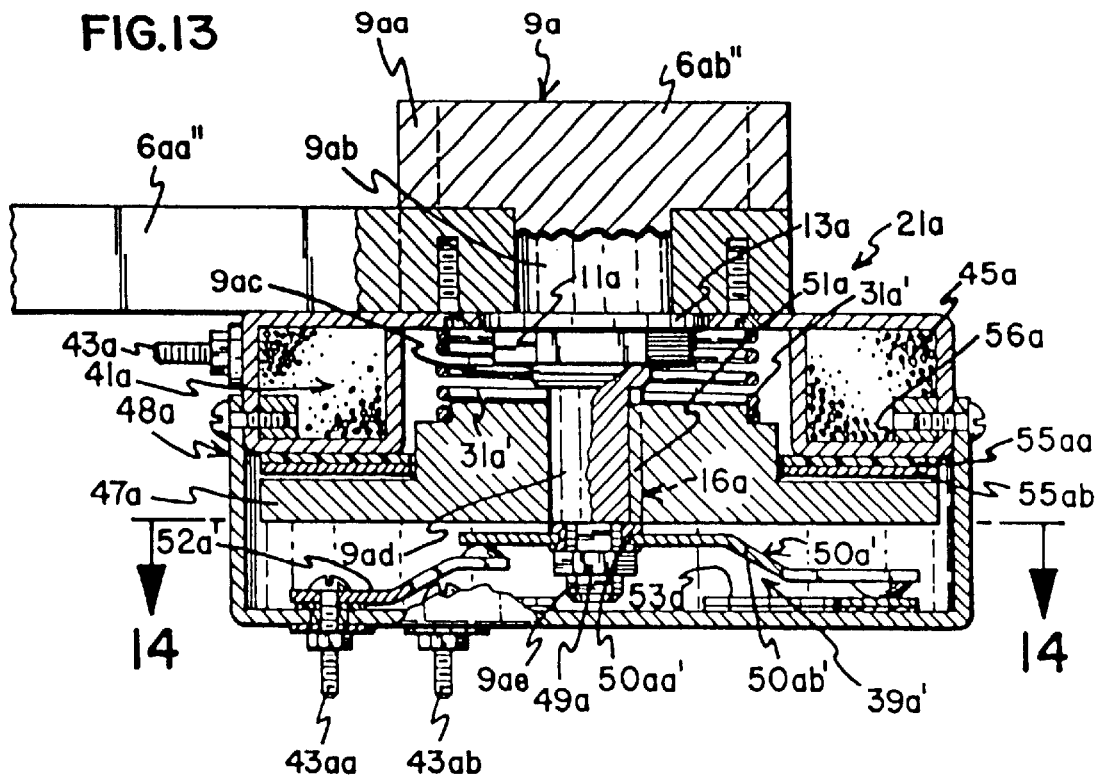
FIG. 13 is a sectional view of the electromechanical hinge shown in FIGS. 11 and 12 from the line 13—13 of FIG. 12.
Figure 14:
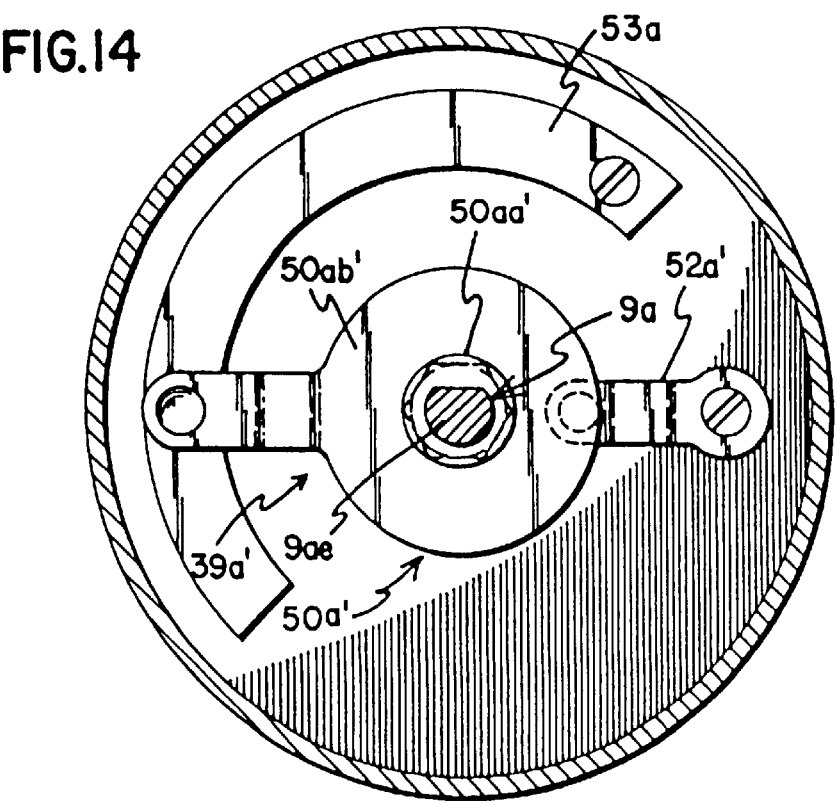
FIG. 14 is a sectional view of the electromechanical hinge of FIGS. 11 and 12 as seen from the line 14—14 of FIG. 13.

Referring now also to FIGS. 11–14, yet another embodiment of the present personal orthopedic restraining device 2" includes a pair of electromechanical hinges 21a and 21b which are incrementally adjustable. This embodiment of the restraining device 2" can include all of the elements of the restraining device 2' shown in FIGS. 3 and 4, except that the incrementally adjustable hinge apparatus 20a and 20b have been replaced by the electromechanical hinge 21a and 21b, which are mirror images of one another. The elements of the electromechanical hinge 21a are shown in FIGS. 13 and 14. The electromechanical hinge 21a is also an incrementally adjustable hinge and includes an alternate potentiometer-like mechanism 39a' which is part of an alternative position sensing device 60' (not shown) for sending an output to a control unit 10", and also includes other elements corresponding to similar elements included in the adjustable hinge apparatus 20a. In the preferred embodiment shown in FIGS. 11–14, the electromechanical hinge 21a is partially controlled by the control unit 10".

The electromechanical hinge 21a includes an electromechanical brake and/or clutch mechanism 41a similar to those which are standard in the art. The preferred electromechanical clutch mechanism 41a is interconnected with the control unit 10" by lead wires extending from leads 43a which are electrically interconnected with a stator coil 45a within a stator housing 56a which is designed to attract a magnetically attractable armature 47a when a sufficient magnetic field is created by an electric current passing through the stator coil 45a. The current is derived from a source of electricity within the control unit 10". Separate lead wires connect the potentiometer-like mechanism 39a' of the position sensing device 60' (not shown) to the control unit 10" so that the electrical output, which provides an indication of the angle between the respective distal end sections 6aa" and 6ab", can be monitored and/or recorded by the control unit 10'.

The electromechanical hinge 21a shown in FIGS. 11–14 includes a clutch housing 48a which is secured to the first distal end section 6aa" or 6ba' of the respective elongated restraining bar 6a". A similar hinge 21b is incorporated into the other restraining bar 6b'. In FIG. 13, a cross-sectional view of the electromechanical hinge 21a interconnected to the elongated restraining bar 6a" is shown. The second end section 6ab" is an integral unit including an extended restraining bar segment 7a and a shouldered pin or bolt segment 9a. The shouldered pin segment 9a includes a plurality of pin portions 9*aa*, 9*ab*, 9*ac*, 9*ad* and 9*ae*. The first pin portion 9*aa* is integrally connected to the proximate end of the extended restraining bar segment 7*a*. Together with the second pin portion 9*ab*, the first pin portion 9*aa* defines a first shoulder upon which the first distal end section 6*aa*" can rest as it turns about the second pin portion 9*ab* when the respective distal end sections are allowed to pivot with respect to one another by the electromechanical hinge 21*a*. The third pin portion 9*ac* has a threaded exterior for receiving a nut hla for securing the first distal end section 6*aa*" to the second distal end section 6*ab*" over the shouldered pin segment 9*a*. The nut 11*a* secures a washer 13 against the first distal end section 6*aa*", such that the first distal end section 6*aa*' can turn freely about the second pin portion 9*ab* when it is permitted to turn by the electromechanical brake/clutch. The fourth pin portion 9*ad* is received by an opening (not shown) in the magnetically attractable armature 47*a*. The armature 47*a* includes a spline 51*a* which fits into an armature groove 16*a* for receiving the spline 51*a*, located in the fourth pin portion 9*ad*, so that the armature 47*a* will only turn in a common rotary movement with the shouldered pin segment 9*a*. The fourth pin portion 9*ad* and the fifth pin portion 9*ae* define a fourth shoulder against which a wiper arm 50*a*' is secured. The fifth pin portion 9*ae* includes a threaded exterior for receiving a second nut 49*a* which secures the wiper arm 50*a*' against the fourth shoulder. The fifth pin portion 9*ae* also includes a flat side which provides a key to turn a molded insulating element portion 50*aa*' of the wiper arm 50*a*' which is bonded to the conductive element 50*ab*' thereof. The insulating element 50*aa*' is made of a suitable polymeric material which insulates the shouldered pin segment 9*a* from the electrical current which normally flows through the conductive element 50*ab*' of the wiper arm 50*a*'. This is essential to the integrity of the potentiometer circuit. Because the wiper arm 50*a*' is keyed to the fifth pin portion 9*ae*, it will turn in a common rotary movement with the entire shoulder pin segment 9*a*. As the wiper arm 50*a*' turns, it remains in contact with a contact arm 52*a*' which is connected to one of the leads 43*aa* which is in turn electrically interconnected with the control unit 10". The other lead 43*ab* is interconnected with a resistive slide line element 53*a* and also with the control unit 10". The potentiometer like mechanism 39*a*' is electrically interconnected with the control unit 10" to provide an output to the control unit 10" which can be calibrated to indicate the relative position of the contact point between the resistive slide line element 53*a* and the wiper arm 50*a*', and also the angle between the respective distal end sections 6*aa*" and 6*ab*" of the restraining bar 6*a*'.

The electromechanical break/clutch mechanism 41*a* of the electromechanical hinge 21*a* can be controlled by pushing either a release or a brake button (not shown) on the control unit 10" which will respectively free the armature 47*a* to turn with respect to the stator coil 45*a* or attract the armature 47*a* to the stator coil 45*a* thereby preventing the armature 47*a* from turning with respect to the stator coil 45*a*. When the release button is pushed, the armature 47*a* is free to turn with respect to the coil 45*a* and the angle between the respective distal end sections 6*aa*" and 6*ab*" or 6*ba*" and 6*bb*" may be manually adjusted. In preferred embodiments, the change of the angle between the respective distal end sections can be monitored by watching an LCD readout display (not shown) on the control unit 10" as the angle is adjusted. When the angle reaches the desired angle, the brake may be applied by pushing the brake button, wherein a circuit is completed allowing an electric current to pass through the stator coil 45*a*, thereby creating a magnetic field which attracts the armature 47*a* and prevents the armature 47*a* from turning with respect to the coil 45*a*.

When the armature 47*a* is attracted to the coil 45*a*, as shown in FIG. 13, a pair of free riding annular disks 55*aa* and 55*ab* are gripped between the armature 47*a* and a stator housing 56*a* within the clutch housing 48*a*. The outer annular disk 55*ab* is preferably made of a suitable metal and the inner annular disk 55*aa* is preferably made of a suitable polymeric material to provide for a smooth gripping action between the respective surfaces and to prevent wear therebetween. The free riding disks 55*aa* and 55*ab* encircle a center portion of the armature 47*a*. A coil spring 31*a*' biases the armature 47*a* away from the stator housing 56*a* when the magnetic attraction between the coil 45*a* and the armature 47*a* is insufficient to overcome the mechanical force of the coil spring 31*a*' which biases the armature 47*a* away from the stator housing 56*a*.

In a preferred embodiment of the present invention, the electromechanical brake/clutch mechanism 41*a* is controlled by a microprocessor 64 (see FIG. 15) in the control unit 10" which is programmed to release the brake/clutch mechanism 41*a* after the completion of a specified number of isometric events or repetitions when the device 2" is set at a specific angle with respect to the respective distal end sections. Upon achieving a required number of isometric repetitions, the programmed microprocessor will release the brake and the angle between the respective end sections can be manually adjusted to a different angle. The program may further dictate how much the angle may be changed prior to breaking the electromechanical hinge 21*a* again and requiring further isometric repetitions at the new setting. In this manner an entire exercise routine can be controlled by the programmed microprocessor. Preferably, the mechanical movement of the electromechanical hinge 21*a* will be generated by force placed upon the device 2" by the individual engaged therein. However, the programmed microprocessor can be designed to place controls upon what movement will be allowed and when that movement will be allowed (i.e., after certain isometric event requirements have been met). It will be appreciated that such a system may be used to create a variety of exercise requirements which an individual will be encouraged to follow by his physician in order to conduct a proper exercise or rehabilitative routine.

Illustrated in FIG. is a functional block diagram of the control unit 10" of the orthopedic restraining device 2" shown in FIGS. 11–14. The control unit 10" preferably controls certain aspects of the operation of the orthopedic restraining device 2". The housing 4" of the orthopedic restraining device is represented by the broken line 4" and the control unit 10" is represented by the broken line 10". The various components of the control unit 10" are illustrated as being suitably electrically connected. The control unit 10" receives analog input signals from the position sensor 60' configured and arranged for sensing the relative angular position of the first and second distal end sections of the orthopedic restraining device 2", and the control unit 10" also receives signals from a stress sensing mechanism, in the embodiment shown the strain gauges 8", for sensing stress on the orthopedic restraining device 2". The signals received from the position sensor 60' are representative of the sensed relative angular position and the signals received from the strain gauges 8" are representative of the sensed stress. In the embodiment shown, control unit 10" shown thus receives two general types of input signals: one representative of the angular position of the orthopedic restraining device 2" and a second representative of the strain on the orthopedic restraining device. The position sensor 60' is suitably electrically connected to an analog to digital convertor 62 which converts analog signals to digital signals. The strain gauges 8" are suitably electrically connected to the analog to digital converter 62. In the embodiment shown, the strain gauges 8" are illustrated as being interconnected to an amplifier 63 for amplification of the output signals from the strain gauges 8". In addition, the amplified signals output from the amplifier 63 are passed through a low pass filter 65 for filtering out background noise and other unwanted signal interference. The signal frequency output from the low pass filter 66 is roughly four hundred (400) hertz ($H_z$). The output from the low pass filter function 65 is transferred to sample/hold circuitry 67 which periodically samples the output from the low pass filter 65 and then outputs the sensed electrical signal value to the analog to digital convertor 62. The electrical connection between the strain gauges 8" in the housing 4" and the amplifier 63 in the control unit are represented by the reference numeral 12" while the electrical interconnection between the position sensor 60' and the analog to digital convertor 62 is represented by the line 61. It will be appreciated that the amplifier, low pass filter, sample/hold, and analog to digital convertor functions 63, 65, 67, 62 might be achieved by conventional well known circuitry.

The control unit 10" is further illustrated in FIG. as including a microprocessor 64. It will be appreciated that numerous microprocessors might be utilized in keeping with the present invention; e.g., Intel 8088 and 8086, Motorola 6800, etc. The microprocessor 64 is shown as including a power supply 66 and a nickel cadmium battery 69. In addition to providing power to the control unit 10" in its operational state, and to a lesser degree, in its idle state, the power supply 66 also provides power to the electromechanical hinge 21, the position sensor 60' and the strain gauge or gauges 8". The microprocessor is also illustrated as including non-volatile data memory 68 for storing data and non-volatile memory 70 for storing a control program. The memory 68 might be low power CMOS memory which can be read and written into and is powered by the battery 69. The memory 70 might be electrically programmable read only memory (EPROM). The control unit 10" is further illustrated as including a real time clock 72 including an alarm function. In alternate embodiments, a speaker and a voice synthesizer might be used to provide voice commands and information to the user. In addition, the control unit 10" is illustrated as including a keypad 74 for user input into the control unit. It will be appreciated that any number of user input devices might be utilized; e. g., a keypad having individual keys, a touch sensitive pad, etc. The control unit 10" is further illustrated as including a graphic liquid crystal display 76 for displaying graphics and text information and suitable user alerts. The display 76 can have various resolutions; e. g., a 240 by 120 pixel display might be used. Once again, it will be appreciated that numerous display apparatus might be utilized in keeping with the present inventions. Additionally, the control unit 10" is illustrated as including a piezo alarm 78 for providing audible alerts to the user.

The control unit 10" is further illustrated as including an ETA 232C asynchronous communications port 80 on the microprocessor 64 for enabling communications with the devices remote from the control unit 10". It will be appreciated that more than one communications port might be present and/or that multiple communication protocols might be utilized. There are several uses to which the communications port capability can be applied. For example, information can be down loaded from the microprocessor memory 68 to a printer/plotter for printout of selected information. In addition, data might be down loaded from the memory 68 of the microprocessor 64 to an external storage device having removable media so as to enable transfer of the data to a remote location. Yet in other embodiments, a communications port might provide for wireless transmissions from the microprocessor 64 to a remote host such as a microcomputer in the doctor's office or clinic. The communications port 80 might provide for interconnection to a modem such that the user patients can down load data into their doctor's computer system by use of to modem from their home or office. Still another application for a communications port would be to enable direct electrical connection between the microprocessor 64 and another computer. This would allow down loading of data from the memory 68 of the microprocessor 64 by interconnecting the microprocessor 64 to a suitable computer. For example, the user patient might come into the clinic on a periodic basis and have a technician connect the control unit 10" to a suitable computer in the clinic and down load the data for analysis by the doctor while the user patient was at the clinic or at some later time. It will be appreciated that while the elements shown in FIG. 15, and discussed hereinabove, are described in terms of the embodiment shown in FIGS. 11–14, similar elements can be incorporated in the embodiment shown in FIGS. 3–10, and also in the embodiment shown in FIGS. 1 and 2 to the degree such elements are individually or collectively applicable thereto.

Figure 16A:
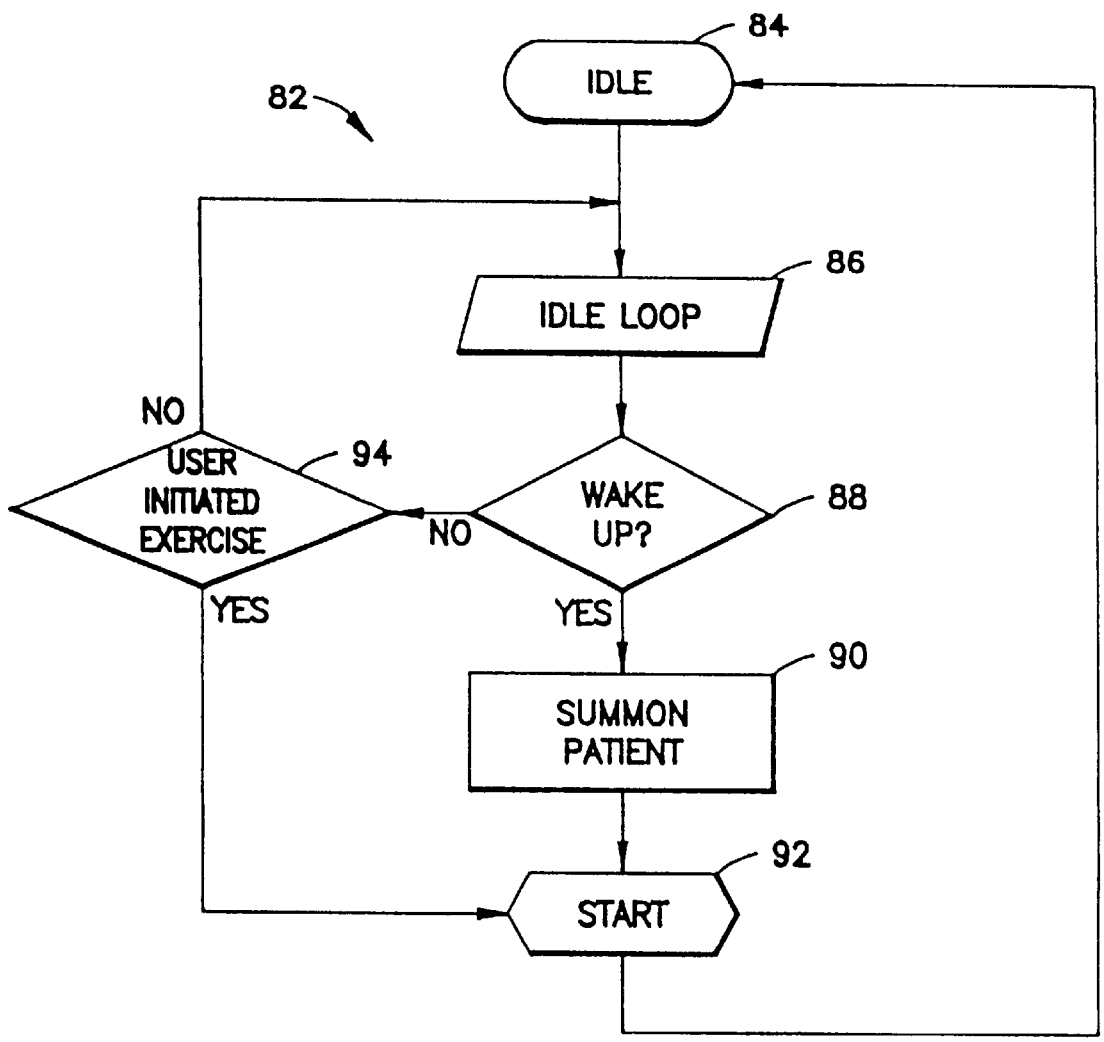
FIGS. 16A through 16C are functional flow diagrams of control logic for an orthopedic device in accordance with the principles of the present invention.
Figure 16B:
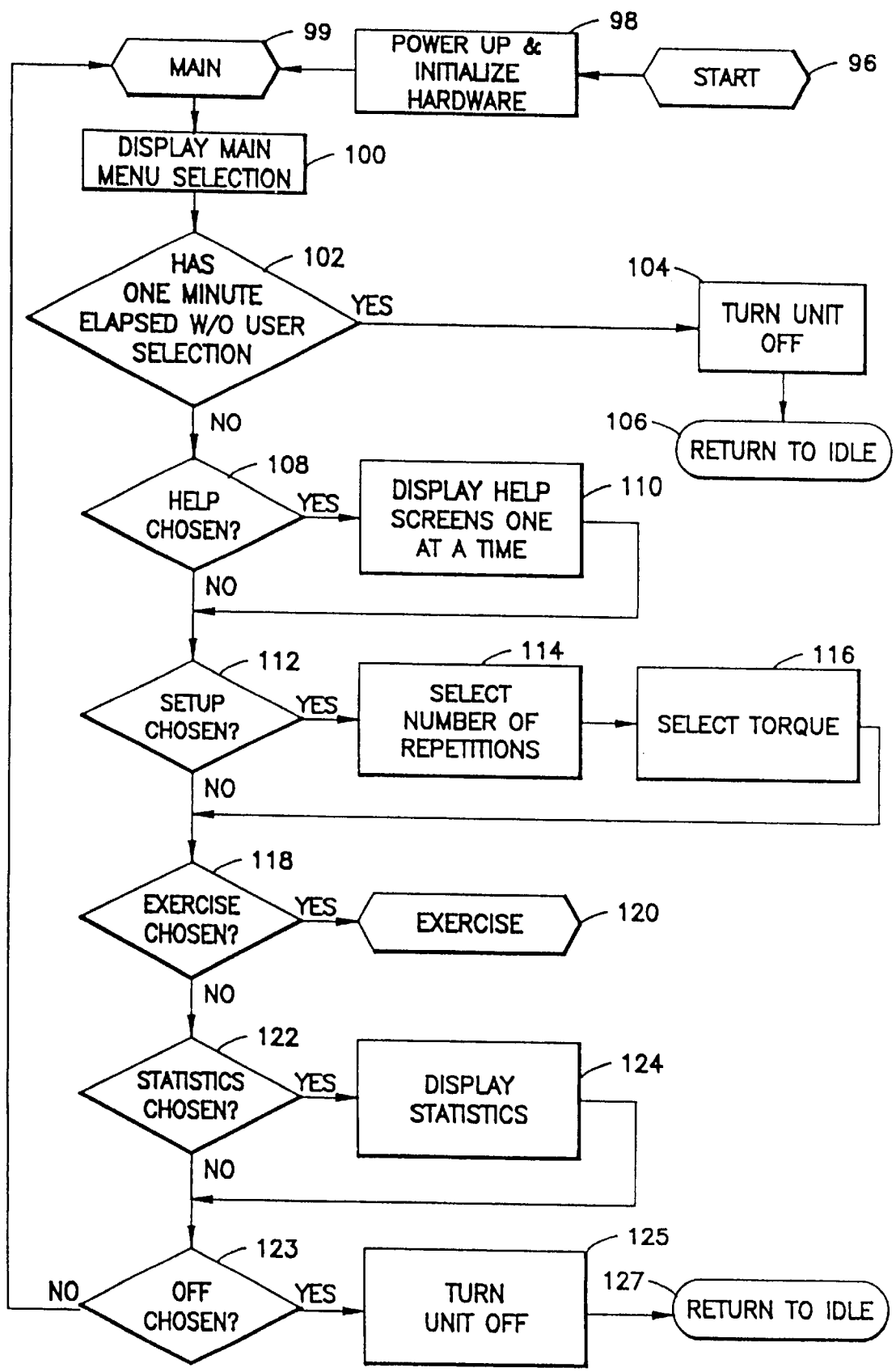
Figure 16C:
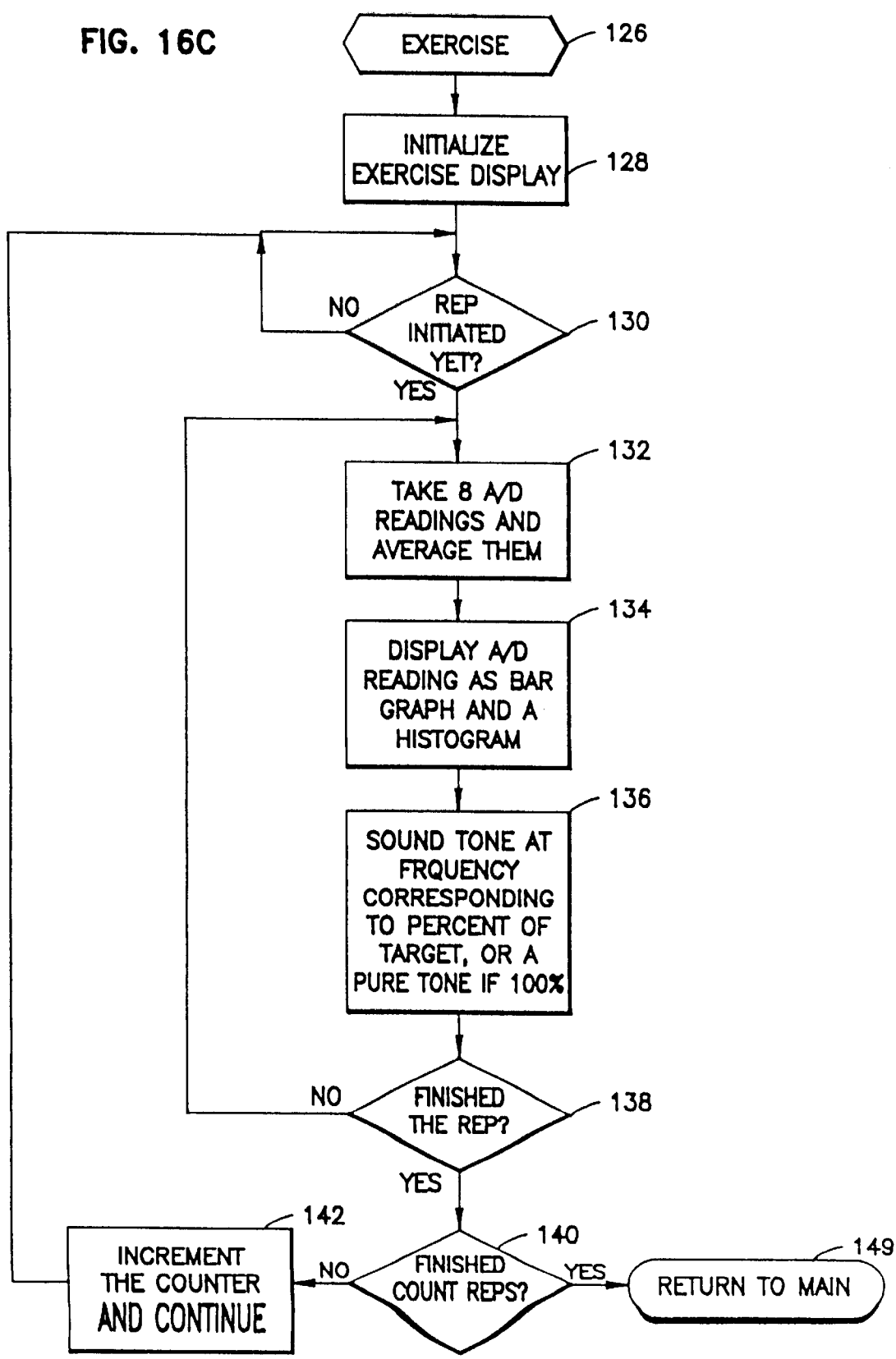

Referring now to FIGS. 16A through 16C there is illustrated a functional flow diagram of control logic for an orthopedic device in accordance with the principals of the present invention. It will be appreciated that numerous embodiments of the control logic might be implemented and yet be in keeping with the principals of the present invention. Moreover, various levels of capabilities and features can be incorporated into the control logic so as to provide the orthopedic restraining device 2" with a wide range of features and applications. In the embodiment shown, the control logic is embodied in a control program 82 stored in the memory 70 of the microprocessor 64. In the embodiment shown, thirty-two kilobytes (32 kB) of memory storage is used for both data and the control program 82.

During typical operation, the control unit 10" will be in an idle state requiring minimal power. During this idle state, the control program 82 will periodically check the real time clock 72 to see if the elapsed time is such that it is time for the user patient to exercise. This is best illustrated in FIG. 16A wherein the control program starts at block 84. At block 86 the control program will go into an idle loop for a predetermined period of time. A check is then made at block 88 to see if the elapsed time is such that it is time for the user patient to exercise. If this is the case, then at block 90 the control program 82 will summon the patient by use of an audible, palpable and/or a visual alarm. The audible alarm might be executed by use of the piezo alarm 78 as illustrated in FIG. 15. The visual alarm might take the form of a flashing indicator or the like on the display 78. A palpable alarm could take the form of a common electromechanical vibrator 77. After summoning the patient at block 90, the control program 82 at block 92 then calls on a start subroutine illustrated in FIG. 16B. At block 88, if it is not yet time to summon the patient, the control program 82 at block 94 checks to determine if the user patient has initiated an exercise. If at block 84 the user has requested initiation of an exercise then the control program 82 calls on the start subroutine at block 92. However, if the user has not initiated an exercise, then the control program 82 returns to the idle loop. It will be appreciated that in some embodiments of the present invention, both of the function represented by blocks 94 and 88 may not be present. For example, if the doctor does not want the patient to initiate his/her own exercise, the function represented by block 94 might be deleted from the control program 82. In this case, at block 88, if it is not yet time to summon the patient, the control program once again returns to the idle loop 86. In yet other embodiments, the user patient might be allowed to initiate exercise only if the torque (foot pounds of force) selected by the user patient to be applied by the user is within a predetermined limit. If this were the case, there would be an additional logic clock to see if the related torque was within the guidelined limit. It will be appreciated that various alternative scenarios might be utilized and still be in keeping with the principles of the present invention.

The control logic for an embodiment of the start subroutine 92 is illustrated in FIG. 16B. The start subroutine begins at block 96. At block 98 the control unit 10" powers up to a full operational power level and initializes the hardware including the sensors of the orthopedic restraining device 2". At block 99, the control program 82 enters a subroutine named MAIN which is a menu display subroutine for displaying various menus on the display 76. At block 100 a main menu selection displaying various user patient options/modes of operation is displayed on the display 76. In the embodiment shown, the following options are displayed as the main menu: Help, Setup, Exercise and Statistics. The control program 82 then checks if the user patient has made a selection within a predetermined period of time; e. g., one minute, at block 102. If no user patient selection occurs within this predetermined time interval, the control program 82 then turns off the control unit 10", i.e., powers the control unit 10" down to its idle state, at block 104. At block 106 the control program 82 returns to the idle state and will remain there until it is time to summon the user patient for a scheduled exercise or until the user patient initiates an exercise. At block 108 a check is made if the user patient has selected the help option. If the user has selected the help option, then at block 110 the control program 82 displays the various help screens one at a time. The help screens will provide the user patient with the information necessary to operate the control unit 10". If the help option was not selected by the user at block 108, then at block 112 the control program 82 checks to see if the user patient selected the setup option. If the user patient has selected the setup option at block 112, then at block 114 the display prompts the user patient to select the number of exercise repetitions, which the user patient does at that time.

At block 116 the display prompts the user to select the force (torque) to be applied, which the user does at that time. In alternate embodiments, the force (torque) to be applied is preset by the prescribing professional. The number of repetitions and torque preferably have a default value which is preset by the doctor or prescribing professional. In some embodiments, after being preset, the user will not be able to change these default values. It will be appreciated that various parameters and restrictions might be placed on the setup functions of the control program 82. For example, the patient might be allowed to select from within predetermined parameters the number of repetitions and the force (torque) to be applied. The control program 82 might be programmed to vary the number of repetitions and force (torque) requirement throughout the user patient's recovery/exercise term. The setup options might be limited such that the patient can only select additional exercise and not less then that prescribed by the doctor. Moreover, the patient might be forced to select within a range of force (torque) values. In the preferred embodiment, the orthopedic restraining device 2 has an operational torque range of from zero to one thousand foot pounds. It will be appreciated that, in alternate embodiments, this range might vary depending upon the joint being exercised and/or the parameters specified by the healthcare professional. The keypad 74 will preferably include numeric keys, direction keys, and other predetermined function keys such as an enter key to enter the selected value. The selected number of repetitions, number of exercise times per day, time of day to exercise, etc. might be selected by using up, down, and sideways keys with the enter key being used to enter a selected value into the system.

Next the control program 82 checks to see if the exercise option is selected by the user patient at block 118. If the exercise menu is selected at block 118, then at block 120 the control program 82 calls on an exercise subroutine, an embodiment of which is illustrated in FIG. 16C. If the exercise option is not chosen at block 118, then at block 122 the control program 82 checks if the statistics option is selected, by the user patient. If the statistics option is chosen by the user patient, then at block 124 various statistical information is displayed on the display 76 with sensed stress data obtained from a prior exercise. If the statistics option was not chosen at block 122, then at block 123, the control program 82 checks to see if the user patient has selected the off option so as to exit the menu display subroutine. If so, at block 125, the control program 82 powers the control unit 10" down to its idle state. At block 127, the control program 82 returns to the idle state. The control program 82 will then return to displaying the main menu at block 99. It will be appreciated that numerous types of statistical displays might be provided to the user on the display 76. For example, a curve might be displayed wherein the area under the curve represents the work done (total energy exerted) by the patient during a particular exercise cycle. Yet another type of statistical display might be a display of the variance between the exercise goal and the actual exercise accomplished. Moreover, much more elaborate statistical analysis might be provided at a host computer such that upon down loading the data from the control unit 10", the host computer can provide a number of different statistical analyses.

An embodiment of the exercise subroutine is illustrated in FIG. 16C the exercise subroutine begins at block 126. At block 128, the control program 82 initializes the exercise display presentation which is displayed on the liquid crystal display 76. At block 130, the control program 82 checks if the user patient has begun an exercise repetition. This is determined by sensing a force (torque) being exerted by the user patient in the proper direction. Once the user patient has started a repetition at block 132 the control program 82 will take a predetermined quantity of signal readings as received from the analog digital convertor 62 and average them. At block 134, the control program 82 will display the readings from the strain gauges as the strain sensed by the strain gauges 8. In one embodiment, the signal readings are averaged. The averaged signals are then displayed as a bar graph or a histogram on the display 76. At block 136, the control program 82 sounds a tone at a frequency corresponding to a percent of the targeted exercise force (torque) be exerted by the user patient and will sound a continuous tone if the user patient achieves the targeted exercise force. At block 138 the control program 82 will check to see if the user patient has finished a particular repetition. If not the control program 82 will continue to take readings and averaging them. If the repetition is finished, then at block 140, the control program 82 will check if the user patient has completed the number of repetitions designated by the doctor and/or selected by the user patient. If the user patient has not finished his/her repetitions, then at block 142 the repetition counter is incremented and the control program 82 continues taking readings. Between repetitions, the control program 82 calculates the work or energy exerted by the user patient and might display the energy exerted as a percentage of the targeted energy amount. Stress data obtained during the exercise is saved or recorded for subsequent statistical analysis, displaying, recording and/or downloading to another computer. If the user patient has finished the designated number of repetitions, then at block 144 the exercise program 82 returns to the start program in FIG. 16B at the location where it initiated the exercise program such that the start program continues its normal execution and will check at block 122 to see if the statistics option was chosen.

From the above discussion it will be appreciated, that the control unit 10" might have various levels of functions. In the most basic configuration the control unit 10" might simply indicate sensed stress, display data and/or store data. Additionally, although in the preferred embodiment of the control unit 10" mounted on the housing 4" includes all the features shown in FIG. 15, it will be appreciated that some of these features might not be present and/or that other features might be contained in a separate ambulatory housing which is interconnected to the control unit 10" when desired. For example, the keyboard and display features might be present in a separate hand held housing. Alternatively, the entire control unit 10" can be wired or wirelessly interconnected for receiving outputs from the strain gauge or gauges 8", and/or other elements of respective embodiments of the present restraining device, only when desired by the user.

A primary problem in orthopedic surgery is the complexity with which weakness, muscle weakness in particular, compounds pain or other injury. A person who has, for example, a patellofemoral problem may be able to tolerate the pain which the patellofemoral problem causes, but they cannot tolerate the long-standing weakness which results from a patellofemoral problem, especially when that complicates the pain. The person in this circumstance is then in a double bind. They cannot use the knee for active daily living because it is weak, and they cannot do exercises to strengthen the knee because it is painful.

The concept behind the present invention is the separation of motion from pain so that effective exercise can be accomplished. In the example discussed immediately above, exercise is performed with the knee at rest, taking advantage of the knowledge that an isometric exercise performed at a series of different degrees of flexion will result in effective strength improvement throughout the entire range. This basic concept is applicable to other joints as well, including but not limited to the ankle and elbow.

In order to gain a fuller understanding of the problem and the proposed solution, we will continue with a discussion of a patient who has sustained an injury to the anterior cruciate ligament of his or her knee. A specific twisting mechanism ruptures a ligament within the knee; some bleeding and pain result. Common treatment for this injury is to immobilize the entire knee in an attempt to protect the knee from (1) further ligament injury; and (2) the pain and disability which result from the secondary swelling and fluid collection. However, total knee immobilization will result in deterioration or disuse changes in the muscles, connective tissues and surrounding bone. Strictly speaking, immobilization of the knee is unnecessary so long as the ligament is not further damaged. Therefore, what is really necessary is to maintain control of the knee while it is being exercised. It is for this reason the present proposal is advanced.

A further example is illustrated by a six-year old child with a long oblique fracture of the distal tibia. This fracture must be immobilized and protected from weight bearing. However, because of the nature of a child, simple instructions to avoid bearing weight on the leg, can go unheeded, thereby resulting in possible deformity and disability. A device to remind the child that such stresses are not allowed would be very helpful. If the present invention is provided with a load cell to sense such a load, a signal from a control device interconnected with the load cell could be programmed to alert the patient and/or the physician that inappropriate stress has been placed on the leg. Data from the load cell can also be recorded. The device 2 shown in FIG. 1 includes such a load cell 14 which can have the specific characteristics of any of the commonly available commercial load cells.

Another example would be an isolated medial collateral ligament tear of the knee. This is inherently a stable injury when appropriately protected. Some motion would be allowed and some muscle contraction would be allowed. However, at this time, no method is known to both support the extremity and provide the patient and doctor with enough feedback to allow cautious, protected strengthening and motion exercises to proceed.

An additional example would be an upper tibial fracture or osteotomy. If this were of the stable type, it would be surrounded by healthy tissues and healthy muscles at the outset of the injury or surgery, and motion and strengthening exercises could be allowed. What is currently keeping a patient from doing such motion and strengthening exercises is the lack of a sophisticated device to both maintain position and to monitor strengthening exercises.

An upper tibial fracture theoretically could be formed in several ways. It could open like a book, it could be distracted, or it could rotate one fragment upon the other. Current treatment for this injury is to immobilize the extremity in a cast. This prevents translation and rotation, and the normal muscle contraction prevents distraction of the injury.

The ankle is a similar situation. The mortise of the ankle is actually a stable configuration. There is a buttress medially and laterally, and there is a curved surface into which the talar dome fits snugly. A person who inverts or rolls on the ankle may tear the ligaments on either side but normal muscle tension prevents translation of the talus. This is because the talus sits within these conforming structures. Treatment for such an injury is to immobilize the entire extremity in a cast. This results in atrophy of the calf muscles, atrophy of the surrounding bone, weakness and probably some slower healing of the injured ligaments. Clearly such strict immobilization is not necessary and probably is detrimental. It would be much preferable if such an injured ankle could be placed in a device which would both support the injury, encourage cautious protective motion or strength and finally monitor the degree of motion or strength as it occurs and any gains which may result from exercise.

It is known that bone should be exercised. It is believed that weight bearing applied to certain healing fractures may cause the fractures to heal faster and more predictably than if the fracture is not stressed at all. Similar responses are also believed to be expectable for connective tissues such as ligaments and articular cartilage.

Following his or her evaluation of an injury or disability, the doctor or prescribing professional makes a determination as to whether or not exercise will be allowed. Exercise is allowed when it is known that the injured tissue is stable and that exercise can be performed in a controlled manner. The problem which arises is that the physician or prescribing professional does not have adequate data to be assured that proper control can be maintained. The amount of force the patient can exert voluntarily is unknown and mechanisms for monitoring the exertion of force have, heretofore, been inadequate or nonexistent.

There are also injuries which are unstable. The cast applied to an unstable fracture cannot always protect it from deformity and collapse. Comminuted fractures of the tibia are an example of this. Such a proposed device would not apply to comminuted fracture of the tibia or similar injury unless it would be to surrounding structures which could safely be moved or exercised. The converse of such a device may be useful in that it would detect unwanted strains or stresses placed upon a potentially unstable injury reminding the patient and protecting from deformity which might otherwise occur.

The simplest and crudest method of protecting an injury at this time is the cast. This allows no movement, it allows no strengthening and it provides no data to the physician or patient. The cast is used when motion is not allowed, it is true that motion is most physiological for connective tissues but it is not always possible when control of the healing injury is necessary. Casts are associated with what is called cast or fracture disease. this is weakness of the muscles, atrophy of the muscles and bond and stiffness of the related joints. Some of these problems may be permanent. Other problems with cast immobilization include a possibility of developing phlebitis (the formation of blood clots), pressure sores or skin pressure changes. The resulting atrophy of connective tissue muscle or bone proximate the joint or injury, further results in weakness and/or stiffness of the joint and, finally, pain. It is not comfortable to have an extremity unnecessarily immobilized in a brace.

The next simple step in the mobilization of injuries has been to add a hinge to a cast. This does allow movement but it does not allow the patient to perform any strengthening and again it has not provided the patient or physician with any data. It would therefore be helpful if a cast brace could be instrumented in such a way that stresses within the brace could be monitored. It has always been a problem that the patient could not make the distinction between exercising the extremity without motion but still derive thee benefits of exercise as if it had been performed with motion. The joint can be moved carefully but it cannot be moved forcefully.

Another example would be the debility and pain which follows a meniscus tear. The meniscus normally is a wedge-shaped structure which sits within the knee. It moves out of the way with flexion and extension of the knee. This, however, cannot occur if there is a tearing of the meniscus or some other type of joint damage. This tear of the meniscus results in pain, mechanical blockage or possibly retearing and further injury. Therefore, when the patient attempts to rotate the femur against the tibia, the tear in the meniscus results in abnormal joint stresses and possible further injury. The same problem exists following repair of such a torn meniscus. The patient attempting to move the knee under unprotected and unmonitored conditions may redisplace the sutured meniscus tear. On the other hand, the knee may be able to bear the weight of certain types of exercise without motion or it may be able to bear the motion of certain types of exercise without weight or compressive force even though, it cannot bear the compressive forces and the motion together. There are two components of exercise, compressive force and motion. The present method would assist the patient to separate these two components.

An additional problem exists within the failure of longitudinal structures. A patellar tendon, for example, if it is disrupted, is not adequately protected by surrounding the leg with a cast. It is a common problem in patellar tendon disruptions (or quadriceps disruptions or similar injuries) that the patient will attempt to move the extremity with a contraction of the associated muscle even though the tendon is damaged. This can result in further damage or can result in disruption of an attempted repair. At this time, it is simply suggested to the patient and they are reminded that they should not attempt to elevate the extremity. However, this is often not adequate. Normal reflex mechanisms cause the quadriceps muscle (in this case) to contract with hundreds of pounds of force which can cause these casted repairs to disrupt in the cast. For this reason, then, a device is necessary which could remind the patient that the extremity is being stressed in an impermissible way. It needs voluntary protection but it can only get that protection if the patient understands and is reminded in some way that the stresses are occurring.

An additional problem is that which results from the collection of blood within an immobilized extremity. Blood clots result and sometimes embolize to the lungs, creating serious medical problems. It would be of benefit to the patient if some type of reminding device could be placed in the cast or adjacent to the cast so that they could be reminded to exercise the calf muscle (in this case) pumping the blood, maintaining flow and preventing some of these serious medical problems. This could be done with certain types of stable injuries.

Oftentimes, the patients simply forget to do the exercises which are considered important. Patients are distracted by their activities of daily living and it is simply possible to forget about the extremity within the immobilization. When it is determined that exercise within protection is necessary, it would be most effective if the patient was both reminded by the protecting device and monitored as they execute the necessary activity.

It is known that patients who have fracture of the distal radius, adjacent to the wrist, may have long-term stiffness resulting from the immobilization of the fracture itself. In other words, if a patient has a wrist fracture and a cast only goes to the wrist leaving the fingers exposed, because of swelling which results from the injury, because of the pain which prevents active use, because of the forgetfulness of the patient and possibly because of the ignorance of the patient in understanding how important most exercises are: permanent stiffness can result. The fracture of the distal radius is particularly common in elderly patients who have osteoporosis. These elderly patients commonly have degenerative changes of the adjacent finger joints and the failure to move these joints during a period of protection (even when the fingers are not immobilized) results in permanent stiffness.

It is possible to use the present device 2 or 2' with the same cast or the same brace and the same treatment plan, but to obtain better compliance with the physician's instructions and better monitoring of the physician's instructions. In addition, such a device will provide documentation of the patient's response and cooperation.

Current casting methods are not simple. It is a complex process which is an art practiced by experts in the art. A cast must be strong, must fit properly, must hold securely and it must not cause any local problems such as allergic reaction and pressure sores. The physician's treatment plan would not have to change much at all. The physician could apply the same type of dressing but with the present device 2, monitor the patient's progress.

In summary, the physician would determine when stress can safely occur. This would be allowed when the injury is stable, when pain is controlled, and if the stress and motion to the area are controlled. Under these conditions, the doctor or medical professional would almost certainly conclude that stress to the tissues can occur safely and should be permitted. Controlled stress to injured tissue has been shown to result in facilitation of healing, less muscle atrophy, and the prevention of scar tissue with maintenance of normal, healthy connective tissue. Current methods have often failed. Rehabilitation is often forgotten while a patient is in a cast. The cast immobilizes the patient unnecessarily, resulting in atrophy, tissue damage, debility and stiffness.

The simplest solution to address these problems would be to provide a cast with elongated restraining bars, a strain gauge and some type of recording device. The device 2 would include a strain gauge 8 interconnected to an electronic monitoring or control unit 10. The electronic monitoring or control unit 10 would preferably allow the patient and the physician or therapist to monitor the following:

1. Maximum stress exerted.
2. The quality and duration of contraction.
3. The improvement of the person's strength over time.
4. Any unwanted movement (if flexion was occurring when only extension was desired or when translation of the bone was occurring when protection from translation was desired).

Strain gauges function through monitoring the electrical resistance of the tiny circuit. The kit could be applied in such a fashion to a cast that minute deformation of the cast could be monitored. These minute deformation which occur in even otherwise apparently rigid structures could be calibrated so that a person attempting to perform knee extension exercise to strengthen the quadriceps muscle could do so reliably either maximizing the contraction in the case of a stable injury or protecting from an excessive contraction in the case of a less stable injury. Again, the physician would be able to decide whether or not the injury is stable but now the physician has more adequate control because he has more useful data. The ideal device 2, therefore, would provide the information necessary for control as well as encouraging the exercise to occur, perhaps through some type of reminding device. The instrumented cast device 2, therefore, would result in better patient compliance, less debility and an overall smoother course of rehabilitation and healing.

As has been mentioned above, the simplest device 2 would be an instrumented cast. This would allow the patient to perform an isometric contraction at a fixed degree of flexion when it is determined that motion cannot be allowed. A second device 21 would allow the patient to vary the flexion points at which exercise is performed. It is believed that this would be desirable given the research findings presented below which are generally attributable to the literature cited:

"The isometric exercise performed at an angle of 15° of knee flexion resulted in the average increase of 32 percent of the torque obtained at the corresponding test position (0.01)." Lindh, M., 1979, *Scandinavian Journal of Rehabilitation Medicine*, Vol. 11:331–36.

"Exercise performed at 60° did not significantly increase the strength of the 15° angle." Lindh, M., 1979, *Scandinavian Journal of Rehabilitation Medicine*, 11:33–36.

It is believed that the ideal immobilization would be some type of adjustable and conforming brace which could be set to allow either no movement or only some certain movement. Such braces tend to be more comfortable than casts, more compliant, and with optimum design, should permit the same type of immobilization as obtained with a cast. The cast does not have the same advantage, however, because it cannot be modified to allow motion.

Other researchers who have studied related problems report the following findings:

There is a "position-dependent" effective isometric exercise. In other words, a patient who contracts the muscle in a fixed position will get strengthening at that position and at nearby flexion points. (These findings mainly agree with those of other authors who suggest that position-dependent isometric exercise is effective.) (Lindh, M., 1979, *Scandinavian Journal of Rehabilitation Medicine*, Vol. 11:33–36.

"Even a maximal static contraction voluntarily initiated is visualized as a neuromotor coordination capable of being influenced by motivation and a variety of other factors." Henry and Whitley, *The Research Quarterly*, Vol. 31 (1).

Isometric exercise improves dynamic strength at a low velocity but not at a high velocity. Lindh, M., 1979, *Scandinavian Journal of Rehabilitation Medicine*, Vol. 11:33–36.

"It is consistent with the hypothesis that strength in action is controlled by neuromotor coordination centers of the nervous system and, hence, should exhibit the same high degree of specificity that is found in other types of neuromotor performances." Henry and Whitley, *The Research Quarterly*, Vol. 31(1).

"The bulk of the evidence indicated that substantial strength gains could be obtained by the practice of isometric exercises of short duration." P. J. Rasch, 1961, *Journal of the Association for Physical and Mental Rehabilitation*, Vol. 15:46.

It was suggested that the isometric exercise would preferably be performed at different knee angles to secure an optimum total in strength increase. Lindh, M., 1979, *Scandinavian Journal of Rehabilitation Medicine*, Vol. 11:33–36.

"There is no such thing as a purely isometric contraction." P. J. Rasch, 1961, *Journal of the Association for Physical and Mental Rehabilitation*, Vol. 15:48.

In view of these findings it is believed that: (1) a patient benefits in both neuromuscular coordination and in absolute strength gains if exercises are done; and (2) if the isometric exercises are performed in a controlled fashion, the patient can derive benefit from those exercises, optimally the isometric exercise should be done at various degrees of joint flexion so that strength can be gained throughout the entire arc of flexion. This is because of an overlap phenomenon. Exercises performed at 45° also results in some improvement in strength at 30° and 50°, but probably not at points of flexion far beyond those where exercise is performed. This means that this proposed device, which would allow exercise throughout the entire range of motion (isometric, under control, monitored, with feedback to the patient and memory to the doctor) would benefit the patient by allowing them to perform exercises that they do not perform under current methods because of voluntary compliance problems, pain, lack of appropriate data which would allow inadequate monitoring and expense. Currently, patients are sent to physical therapy for instruction and monitoring. It is quite conceivable that such a device could provide better feedback to the patient, closer monitoring, more control and care more consistent with the doctor's instructions at a lower expense than physical therapy.

The basic underlying nature of these exercises is that they are simple but because of lack of compliance, supervision and feedback, these exercises are not being done and the patient suffers both subjectively in the form of pain and weakness but also objectively in the loss of connective tissue structure and other changes, some of which may be permanent. Some of these problems are life-threatening, such as when a patient fails to perform calf muscle contracting exercises (allowing a blood clot to form which may travel to the lungs). Some are simply debilitating (such as the stiffness which results from elderly degenerative hand joints following immobilization for otherwise simple wrist fractures). Some are not externally visible, such as the bony atrophy, which follows prolonged periods of immobilization. Bone material which is lost in this way, is lost as a result of a form of osteoporosis and may never be replaced. Some of the difficulty will be in the form of pain. A joint which is unnecessarily immobilized is uncomfortable and regaining that motion following a period of immobilization adds more discomfort, all of which is needless. Some of these changes are macroscopic; the visible atrophy of the muscle is apparent even to the casual observer. This should be prevented if at all possible, but some of the changes are microscopic or biochemical such as the loss of bony calcium, or the loss of connective tissue matrix.

In summary, a variety of severe and profound changes follow the needless immobilization of extremities and this proposed series of devices is designed to assist the physician by both maintaining control and providing data which is not otherwise available. This will improve patient care.

There are some additional areas for consideration as the present invention is developed. Consider the following problems.

1. Fifty-year old female who has undergone lumbar fusion stabilized adequately by metal plates and screws in the spine is advised to perform exercises, theoretically 30 foot pounds of flexion extension and side-bending torque are admissable within the limits of the internal fixation. Patient is already resting in a brace but has become dependent on the brace. The patient has no concept of what 15 pounds of isometric contraction against the walls of the brace would be and there is at this time no simple way to explain that to them. An instrumented brace would allow them to perform exercises which are currently not being done. They could do this in a controlled fashion, minimizing pain, weakness and stiffness, speeding their recovery.

2. Twenty-five year old white female with degeneration of the back of her right kneecap. At this time the pain is significant but is not as limiting as the combination of pain and weakness. The weakness has occurred insidiously, slowly, because direct spinal reflex has resulted in quadriceps atrophy. Currently, this patient is placed on simple straight leg raising exercises which clearly are not adequate. They improve her quadricep strength but only near full extension and this strength improvement is not helpful when the patient's knee is flexed as it must be to step off a curb or to ascent or descend stairs. The patient cannot take advantage of the currently available methods of physical therapy strengthening including the use of a Cybex-machine or variant because extension of the knee against resistance aggravates her patellar changes, causing additional pain. This patient needs to exercise the knee at various fixed points of flexion because the patella will not hurt as much if it simply compressed; it only hurts if it is compressed and translated with its injured surface.

3. Sixty-five year old white male with severe degenerative arthritis to the knee has such severe quadriceps atrophy that he cannot undergo the proposed knee reconstruction. He cannot be placed on any exercise machine because this hurts too much. Simple straight leg raising exercises will not provide him the comprehensive form of strength that he needs through the entire dynamic range. This patient clearly needs to be able to exercise his knee in a controlled fashion, taking advantage of the pain relief which an isometric exercise occurs but also benefitting from the control of a proposed device which would allow him to perform quadriceps contractions, monitored adequately, at various fixed points of flexion.

A more complex rehabilitation problem is suggested by an individual with an anterior cruciate reconstruction. Under a common method of rehabilitation, the patient is able to do resistance exercises and a narrow flexion arc between 45° and 90° of motion but is allowed free pass of motion between 10° and 90°. An adjustable device 2' or 2" would allow the patient to lock their knee at various points of flexion between 45° and 90° of motion for the desirable strength there. Such a device could also monitor the maximum output of torque so that it could be maintained at a level consistent with protection of the reconstruction. It could be kept with the patient at home or be incorporated in their regular post-operative dressing so that visits to the physical therapist are unnecessary. The device would remind the patient to do the exercise, lock the hinge at the desired and acceptable degrees of knee flexion (as determined by the treating physician) monitor the quadriceps and hamstring contractions as well as perform the more basic function of protecting the knee from other forms of stress.

In summary, the ideal form of treatment is to rest only the injured tissue and to rest it only as much as it needs to be rested. The ideal would include the concept that other tissues around the injured tissue can be and should be moved and exercised so that their function is altered as little as possible. and that function is restored as rapidly as possible.

The present invention will be further described in accord with the following Examples.

I. THIRD DEGREE MEDIAL COLLATERAL LIGAMENT SPRAIN

The term third degree medial collateral ligament strain signifies complete disruption of the medial collateral ligament. It is a significant injury. The normal hinge motion of the knee is no longer constrained side to side. This is usually treated by a cast or immobilization for three to six weeks (leg is at rest). This treatment program has the disadvantage that the patient's cartilage and muscle are not exercised.

In accord with the present invention an instrumented cast similar to the restraining device shown in FIGS. 1 and 2 would be provided as follows:

Application of a cylinder or long leg cast incorporating two elongated restraining bars, generally as shown in FIGS. 1 and 2, with the knee at approximately 35 degrees of flexion. Each of the elongated restraining bars is equipped with a plurality of strain gauges in the same general configuration as shown in FIGS. 1 and 2. The strain gauges are interconnected with a control unit across the knee of the cast which monitors and records outputs from the strain gauges reflecting minute deformations of the elongated restraining bars and the cast. The control unit will remind the patient to exercise at certain times and will allow the patient to monitor the results of the exercise. The control unit will also process the outputs from the strain gauges to provide the following information: (1) Maximum quadriceps contraction (which initially may be small in light of the patient's pain, but desirable); and (2)

Maximum strain to signify the degree of contraction that the patient is able to exert.

Advantages of such a Device Include but are not Limited to the Following:

(1) It would encourage the patient to begin using the extremity in this very controlled circumstance right away. Some benefit to healing the fracture has been demonstrated once exercise can be accomplished.

(2) A person at the end of a period of cast immobilization would be expected to have more quadriceps strength, less measurable atrophy and some improvement in their low speed extension of the muscle of the knee.

(3) Preferably, the device could be set up to monitor both quadriceps and hamstring function. A second alternate device could also be placed at the ankle for those patients in a long leg cast to exercise the calf, both anterior and posterior muscle groups.

II. PATELLAR TENDON DISRUPTION

Patellar tendon disruption is a special problem in that absolute rest of the quadriceps muscle is necessary. The quadriceps is a very powerful muscle and its tendon, whether surgically repaired or allowed to heal without surgery, should have no tension placed through it. This is because tension may disrupt the healing. It is difficult to prevent the patient from contracting the muscle because it is so normal to do so. Even slight contractions can exceed the amount of allowable force.

This injury is ordinarily treated in a cast or immobilization (with the knee near full extension) to rest the tendon. Such treatment is usually necessary for approximately six weeks with physical therapy to follow.

Treatment for such an injury would include:

Application of a long leg cast including elongated restraining bars, with the knee near full extension. A strain gauge or similar device to detect and warn the patient of unwanted strains coming across the knee. It is desired that the patient not contract the quadriceps muscle, but some patients will do this anyway since it is easy to lift the leg into bed, or lift the leg when they begin to stand. This produces an unwanted contraction of quadriceps muscle, therefore, it would produce unwanted deformation of the cast which could be detected by such a device.

Benefits to the patient: The strain gauge would be placed at the knee to monitor this unwanted quadriceps contraction. The computerized device monitoring the strain gauge would emit some type of warning tone or signal to the individual should they contract the quadriceps muscle against the physician's advice. A patient treated in this fashion would stand less chance of accidentally disrupting their patella tendon. This is particularly important following surgery, when all that may support the repaired tendon is suture. Such sutures cannot hold up against the several hundred pounds of contractile force which the quadriceps muscle may exert.

III. SEVERE BIMALLEOLAR ANKLE SPRAIN

Bimalleolar ankle sprain is an injury of both collateral ligaments at the ankle. The sprained ankle is held together under normal tension by contraction of the anterior and posterior muscle groups but cannot support sideways force (such as one exerts on a twisted ankle) because of disruption of the ligaments. It is usually treated for four weeks in a cast to allow the severe tissue damage to heal. With the prior art method of treatment, weakness of the surrounding musculature may result. It would, however, be desirable to exercise the ankle while it is in the cast.

An instrument cast to treat such an injury would include the following features:

(1) A strain gauge type restraining device including a pair of opposing restraining bars across the ankle joint.

(2) A monitoring device in the form of small electronic circuit which would remind the patient to forcibly extend the ankle (bring the foot up) or plantar flex (push the foot down into the toe point position).

(3) The patient would be reminded at various periods of the day that it would be important for them to exercise the various muscle groups. Some muscle groups such as the peroneal muscle group or posterior tibial muscle group whose functions cannot be isolated to a simple anterior or posterior deforming course could also be encouraged by such a device. The patient treated in such a cast would have the advantage that they will have exercise for their muscles during the course of their immobilization and it would not easily be forgotten that these exercises are necessary and important. The patient would have the benefit of the additional muscle strength at the end of the period of immobilization and further recovery would be hastened.

IV. LONG LEG CAST, ANKLE EXERCISE DESIRED

The patient with a tibia fracture or foot and ankle injury which may be in a long leg cast would be optimally treated if they could exercise the calf musculature (both anterior and posterior musculature) to minimize stiffness and optimize venous flow. Exercise of the musculature has the effect of "pumping" the blood through the veins. This prevents venous stasis and theoretically should lessen the incidence of thrombophlebitis and venous obstructive problems. An example would be a stable transverse distal tibia fracture. Such a person is ordinarily in a significant amount of pain following such a fracture, and would probably be in a cast for three to four weeks before an alternate form of immobilization, either in the weeks before a removable brace or a short leg cast, is appropriate.

A person treated for a distal transverse tibia fracture would be treated in the following manner. A long leg cast would be applied with the knee at approximately 35° of flexion and the ankle at neutral dorsi/plantar flexion. Restraining bars would be incorporated into the cast, and strain gauges would be attached thereto and interconnected to a control unit. The cast could incorporate elongated restraining bars crossing both ankle and knee. In this case, a separate strain gauges would be placed at the ankle in addition to those at the knee. The patient would exercise the ankle when suggested by an alarm mechanism in the form of a vibration or a tone in the cast. The patient would attempt to dorsiflex the foot or ankle in this example; five or ten repetitions upwards, followed by five or ten repetitions downwards. This would cause the deep calf musculature to pump the blood through the veins, the course of which is normally augmented by muscle contraction.

The patient using this device would benefit from it in the following ways:

1. The patient would derive some direct strengthening of the calf musculature by the effect of an isometric exercise in this protected situation.
2. Improvement in the patient's strength would be monitored by the electronic or mechanical measuring device. Such information could be stored over time to develop long-term trends.
3. The patient would likely have less chance of venous stasis and subsequent thrombophlebitis. Calf pumping exercises are commonly used when a patient is recumbent in bed following many types of surgeries such as total hip surgery, and its effect is generally recognized.

Use of such a monitoring device should improve the care of the tibia fracture by minimizing the chances of complications such as thrombophlebitis and maximizing the chance of early rehabilitation through strengthening.

V. STABLE COILES' FRACTURE OF THE WRIST

Colles' fracture is a transverse fracture of the distal radius, usually defined as within two inches of the distal joint surface. It is a common fracture and often results from a fall on the extended forearm. Patients are often immobilized for a period of six weeks following such an injury. Very few other forms of protection and treatment are available. Stiffness in the wrist and weakness of the forearm musculature are common problems following treatment of Colles' fractures. Stiffness of the hand and fingers is a problem as well.

The patient treated in an instrumented cast or restraining device of the present invention would have either a long arm or a short arm cast applied across the wrist for this fracture. A restraining bar including a strain gauge of some type would be placed at the wrist, possibly dorsal, possibly volar, possibly radial or ulnar.

The patient attempting to extend the wrist in either palmar flexion or dorsiflexion could be monitored. Certain stable injuries should be very amenable to attempts at forceful muscle contraction. The patient treated in this fashion would benefit from treatment in the following ways:

1. They would tend to have less muscle atrophy because the forearm musculature would be exercised in a monitored fashion within the cast.
2. The patient and physician would have the benefit of monitoring any strength gains by the availability of the direct digital readout.
3. Circulation through the forearm may be enhanced by the pumping action of the forearm musculature.
4. Attendant accessory musculature such as the tendons extending to the fingers, would be exercised as a result of the reminding mechanism. This should forestall much of the hand stiffness which commonly occurs with treatment of these fractures.

VI. MENISCUS REPAIR

A person with a repairable meniscus sometimes undergoes a surgical procedure where the meniscus is sewn back to its bed. The meniscus is normally a c-shaped wedge of tissue which is attached at the outside edge to the ligaments surrounding the knee. Certain types of meniscus tears result in pulling away of the meniscus from its attachment. The meniscus provides a weight bearing function as well as a lubricating function and shock absorbing function within the knee. Disruption of the meniscus is a serious long-term problem. In the past several years, meniscus repair has been advised as a method of preserving its function. This involves a surgical procedure where the meniscus is sewn back, usually by arthroscopy. Twelve weeks of protection for the meniscus are necessary. The first six weeks of this are usually in a cast. The second six weeks may allow motion of the knee, but without weight bearing. The repaired meniscus can bear cautious motion of the knee but cannot bear any motion of the knee under weight bearing. Weight bearing and combination of motion may wrench the meniscus and tear it from its bed.

In accordance with the present invention this person would be equipped with a restraining device or brace including a pair of elongated restraining bars including strain gauges and adjustable hinges. The brace would have a configuration with the following features:

The brace would be applied to the knee, which would be adjustable at various points of knee flexion.

The brace would be applied so that the patient can hold the knee securely at 5 degrees. He may then unlock the hinges and move reset them at some predetermined point of flexion. Such a device would allow points of knee flexion at 5 degrees, 20 degrees, 35 degrees, 50 degrees, 65 degrees, 80 degrees and 90 degrees. A computerized monitoring device would both remind the patient and monitor the contractions as they occur.

The patient would use the device in the following way. At various times through the day, depending upon the literature and the experimental information, the patient will be reminded to perform a series of isometric contractions. The patient would, for example, perform 5 maximum extension contractions (using the quadriceps) with the knee at 5 degrees of flexion. The patient would then disengage the hinges and engage them again and perform 5 more extensions. He or she would work up the degrees of flexion in this fashion, until they had finally reached 90 degrees and done 5 repetitions there. A similar series of contractions could be done for the hamstring muscles.

In this way, the meniscus is protected because there is no motion which might tear the meniscus, but the muscles are being exercised during this period of immobilization and protection. At the end of such a period of immobilization, the patient has benefited from treatment in this device. The patient's knee has been allowed movement, and should, therefore be less stiff. The patient's thigh muscle and hamstring muscle have been exercised and he should have less atrophy of the quadriceps and the hamstring muscle. Based on available information, it is suggested that the patient will have more success and easier rehabilitation from that point when motion is allowed without weight bearing. The patient is allowed to contract the muscles, but the motion and muscle action are done as separate exercises, protecting the meniscus but allowing each component of the rehabilitation to occur.

VII. SEVERE CHONDROMALACIA OR PATELLOFEMORAL DEGENERATIVE ARTHRITIS

The patient with severe chondromalacia or degenerative arthritis of the patellofemoral joint cannot actively extend their knee under resistance. The patella, which is a fulcrum for the quadriceps muscle does not have its normal ability to glide over the femur. In the past, strengthening has been done by extending the knee and lifting it off the bed as one would with a "straight leg raising exercise". The disadvantage of the straight leg raising exercise is that it exercises the knee at one degree of flexion only (full extension) and this is simply not very physiologic for patients who will use their knee at up to 90 degrees of flexion for all activities of daily living, even elementary ones such as climbing and descending stairs.

What is necessary is a method of exercising the knee at all degrees of knee flexion, without causing the patellar and femoral surfaces to rub against one another. Attempts have been made in the past to use isotonic conditioning for this purpose, however, even at low degrees of resistance, this abrasion of the surfaces occurs and pain results so that very little conditioning can occur.

The use of a hinged device similar to that shown in FIGS. 3 and 4 would permit the following:

The patient would engage the hinged brace to the leg and be allowed to exercise their knee only at six points of 5, 20, 35 and 50 degrees etc., up to 90 degrees. The patient would lock at each of these measurements and perform a series of quadriceps contraction. This would be far more comfortable than the conventional method of exercising against a moving resistance, in that no motion would be allowed between the two painful surfaces. It would be far more efficient than simply straight leg raising because it allows the muscles to work at various lengths (at various degrees of motion). The result is that some strength is gained at each of the points of flexion, and this can be translated to activities of daily living.

Patellofemoral pain is a vexing problem. Patellofemoral weakness is a cause and sustaining factor in patellofemoral pain syndromes.

This is best stated by Wild et al. (1982, Amer. J. Sports Med 10(1):12–15):

"The protective mechanisms which patients with these syndromes learn in order to avoid further pain and symptoms of instability usually impair their rehabilitation programs, while presenting a real challenge for the physician and physical therapist. The most important of these pain preventing mechanisms is the reluctance of the patient, whether, voluntary or involuntary to initiate and maintain a strong quadriceps contraction."

This is a quite useful summary statement and outlines the nature of the problem very clearly. If the patients, in fact, do learn protective mechanisms which (a great deal of time) necessitate the avoidance of the contraction of the involved muscle. Some of this may be volitional, because of a sensation of pain. The other may be through a direct reflex arc inhibiting quadriceps muscle.

A number of methods have been attempted to this point to modify the quadriceps program. Many of these are simplistic and based on other principles of physical therapy, including:

1. Modifying the position of other joints, such as ankle dorsiflexion or hip adduction.
2. Use of small wedges beneath the knee to change the quadriceps position.
3. Use of direct electrical muscle stimulation.
4. Addition of weight to the end of the extremity to increase resistance.
5. Beginning the exercise in more flexion to change the mechanics of the resting position.
6. Icing.
7. Hamstring full contraction (Antich and Brewster, 1986, Physical Therapy 66:1246–1251).

Professionals, attempting to rehabilitate the quadriceps muscle, have been constrained by this lack of sophistication. Because we cannot control the knee, we resort to icing, position changes, crude weights, etc. These are rather simple, easily accomplished in a standard clinic situation, and avoid the risk of complication. We have been limited because of a lack of control, continued supervision and feedback.

These prior art techniques demonstrate significant disadvantages and there is data in the literature to suggest that simple addition of weights or position of the leg are not in and of themselves satisfactory. Wild et al. (1982, Amer. Sports Med. 10:12–15) in a very simple study suggested flexion of the knee to 10 to 20° reduced the effect of muscle effort of the vasti to approximately one-fourth of the muscle as demonstrated in full extension of the knee. Wild et al. also suggested that this may have been because of mechanical compressive forces across the patellar articular surfaces. This is in direct odds with the feelings of Antich and Brewster (1986, Physical Therapy 66(8):1246–1251), where they felt that the increased surface area distributing the forces in a partially flexed knee would more than make up for any increased force due to compressive loading. "Simple voluntary extension of a splinted extremity never exhibited the amount of motor unit recruitment observed during either resistant or setting exercises," (Allington et al., 1966, J. Amer. Phys. Ther. Assoc. 46(11):1173–1176).

Wild et al. further noted that some of the modification in the quadriceps strengthening program suggested by Antich and Brewster, would not be useful, noting that with electromyography rotation of the hip and the addition of weight to the extremity did not enhance muscle effort with the knee in full extension.

Ideally, the quadriceps muscle should be contracted with the knee in full extension to relieve all compressive forces on the patellofemoral joint. Unfortunately this does not alter the mechanics or physiology of the muscle to make for optimum strengthening of the quadriceps in a useful range for activities of daily living. There is controversy that modification of the knee may improve the mechanics and physiology of the knee with a strengthening program, but this may be done at the expense of inhibition due to a patellofemoral compression pain and possible reflex inhibition. This alteration of mechanics and joint physiology is necessary to approximate a more useful physical therapy program. It is a huge step in rehabilitation to move from straight leg raises (no stress) to isokinetics (stress and motion). Clearly, this area requires study. However, it does seem quite reasonable that with (A) control of the extremity and (B) monitoring of the patient's improvement, improvement in the patient's cooperation with their exercise program would result from the use of the isometric conditioning device. All of the prior art studies failed to demonstrate any sophisticated or elegant system for controlling the extremity under contraction at various points of flexion. The measurement devices are also simplistic. Often, a rather modest amount of data in a relatively few number of subjects were used.

With as such useful data as there is in the literature and as extensive a problem as patellofemoral pain syndrome is, one might expect that there is still room for improvements in our diagnostic and treatment capabilities. People are still struggling with the question of how best to handle these patients. Practitioners who see these patients ever day are faced with the same frustrating limitations in treatment and education as they were 10 to 20 years ago. The foundation of treatment, a simplistic one, is a combination of quadriceps setting exercise and straight leg raising exercises in extension. Little has been done to change that, in spite of the literature which is available to suggest that more resemblance to daily functional activity is necessary. Since the philosophy on these problems varies from practitioner to practitioner, orthopedists and therapists alike, confusion reigns in the mind of the patient. The confusion comes from ineffective education combined with the pain produced by the program. The overall net result is often a failure for the lack of an effective method of treatment.

The cornerstone of the present invention is the availability of data, not only general data or research data, but data as it obtained on an individual patient. How strong are they? How weak are they as individuals? How can that data be used? Can we protect them, while monitoring them, to help them attain the best possible results. The isometric conditioning device sifts through the abstract variables of understanding, education, self and body image, reflex arc impairment, poor cooperation, poor coordination, scheduling, family commitments, family dynamics, transportation problems, professional/patient relationships, response (or failure thereof) over time, individual pathoanatomy, and other factors to give that patient the absolute best possible benefit of what is known in the literature to help them recover and/or maximize their knee or other joint function. Any one of these factors can be preemptive at preventing the patient's recovery. The isometric conditioning device or orthopedic restraining device of the present invention gives the individual patients the benefit of factual data on their own extremities, their own pathoanatomy, and removes those factors obscuring and preventing their recovery. It gives them a highly refined, accurate, sophisticated, personal device which can protect their extremity. At the same time that it encourages and measures their strengthening, while removing as much as possible blocks to understanding and cooperation. It reduces the impact of the purely mechanical factors of human living such as scheduling.

The device may be either applied in semi-permanent sense to the extremity during the course of acute injury, or applied and removed when an extremity may not need as much protection. Because of the sophistication of its hinge design and electronics, factors of pain, emotional overlay are separated so that they can be dealt with effectively. The orthopedist could have made use of the present invention years ago if the electronic sophistication, hinge design, and mechanical data regarding the knee had been known. Now that the mechanics are understood, the electronics are available and medical practice is sophisticated enough to utilize the capabilities the present invention provides, the present device can be used to provide the optimum patient benefit.

VIII. STIFF PAINFUL RHEUMATOID ELBOW IN THE ANTICIPATION OF TOTAL ELBOW REPLACEMENT

The problems with the person with rheumatoid arthritis is that it affects the elbow and they have a severely painful joint which becomes stiff very easily. The rheumatoid arthritis destroys the joint surface so that eventually bone rubs on bone. This can present a very troublesome creaking or grating sensation within the elbow with attempts at use.

The person with rheumatoid arthritis is also affected by severe weakness since they are not able to use the elbow against resistance. Because of the elbow pain, they tend not to use the elbow at all. This results in significant weakness of the surrounding muscle groups including the triceps and biceps. This puts them at a significant disadvantage should reconstructive surgery be considered.

A hinged type restraining device would be configured in the following way:

The patient would be fitted with a brace, very similar to any long arm brace, a hinge support at the elbow. The hinge at the elbow would be fixed between full extension and perhaps 120 degrees of flexion with locking points every 15 degrees or so. The person would put on the device and perform a series of resistance exercises against infinite resistance (allowing no motion) at these various points of flexion. This would be done based on available medical literature as it relates to isometric exercise at some pre-determined number of times per day, perhaps three to four sessions. Each contraction would be repeated for the flexion group and for the extension group five to ten times or whatever the literature experimentation would suggest would be optimum for efficient strengthening of the muscle.

The patient would get feedback to them telling them what maximum contraction they have been able to elicit, what improvement has been made over the period during which their exercise program has come, how many total repetitions they have done and possibly what the length of the total exercise program has been in days or weeks.

A patient severely affected with rheumatoid arthritis for whom such a strengthening device would be considered would benefit from the program in the following ways:

(1) They would be able to exercise their elbow with much less pain since motion would not be allowed.

(2) They would gain strength in the surrounding muscle groups so that ultimate recovery from any proposed surgery such as a total elbow replacement would go more smoothly.

A patient with strength in the muscles surrounding a joint recovers from surgery on that joint much more quickly.

It may actually be possible that surgery could be avoided if sufficient strength or control of the elbow in some nameless way could be gained. Strength and motion are a cornerstone in conservative orthopedic treatment and surgery can often be avoided if sufficient strength and motion can be gained.

IX. STIFFNESS FOLLOWING TOTAL KNEE REPLACEMENT

The person who has undergone total knee replacement commonly will have difficulty with stiffness of the knee. The orthopedist will usually send the patient to a physical therapist almost immediately following surgery for instruction and coaching in the use of the knee. This is to forestall stiffness. This has the disadvantage of course, that the patient will have coaching, reinforcement, and control only in the physical therapy setting, and many patients will simply not do the exercises as forcibly and vigorously as they would if they had support, supervision, monitoring and reinforcement.

The patient who has stiffness in their knee following a total knee replacement could be placed in the electromechanical hinge device in the following way. The brace would support the thigh and the calf and the hinged portion would be at the level of the knee and would provide the patient with the following information:

The device would tell them immediately at what degree of flexion their knee is at the beginning of the exercise. Active level of comfort for stiff knee is usually around 35 degrees. For the purposes of this illustration, we will use the figure of 35 degrees. The patient is to understand that they will attempt to extend their knee. Following total knee replacement, there is generally no danger limit to either full extension or full flexion, so they will attempt to fully extend their knee. As they do this, the digital readout will tell them that they have reached 30 degrees, 25 degrees, 20 degrees, 15 degrees reaching 14 perhaps 13 degrees. But with this additional feedback they are encouraged to continue reaching for the last possible degree, perhaps reaching 14 or 13 degrees with sustained effort. The patient will then attempt to flex the knee, and it will come easily back to the 30 degree starting point and with effort the patient will be able to flex their knee to perhaps 40 to 60 degrees before pain, stiffness or other limitation may hold them back. With sustained effort and reinforcement coming from the device in the form of direct digital feedback, sounds, bells, etc., the patient may be able to get an extra few degrees of flexion.

This is very much the same type of training and reinforcement which the patient gets at the physical therapists' office and after a period of several days of such active exercise, a person can be expected to maximize their motion, so they will be able to get to 10 degrees or 5 degrees (near full extension) after several days of using such a device, and perhaps flex to 90 or 100 degrees in the opposite direction (as they attempt to flex their knee maximally).

A person who uses such a device would benefit from it in the following ways:

(1) They are saved the expense and inconvenience of having to be seen by a physical therapist as much, since direct feedback and encouragement and documentation of their progress will occur within the device. This could be related to a therapist or a physician over the phone.

(2) They are able to participate more actively, more aggressively in their own therapy since they have a direct feedback, and more progress can be expected.

(3) Since the patient will get more direct feedback and support than they would get through the therapist (if only on the basis of convenience alone) they will be able to do their exercises more frequently with greater net overall effect.

(4) Since the number of repetitions will be monitored and available within the device (as one proposed method of development), it would be fairly evident whether or not the patient is complying with instructions, and whether or not some insurmountable plateau is being reached (which may help the physician with any decisions towards manipulation or other forms of therapy).

RHEUMATOID KNEE STATUS POST SYNOVECTOMY

The person undergoing synovectomy for rheumatoid arthritis is a great risk for stiffness. The synovium, once removed, leaves the underlying surfaces which can form scar tissue. These surfaces can heal to one another, causing mechanical blockage or obstruction of the knee, or they can simply heal with thickened scar which creates a resistance to what should ordinarily be smooth gliding movements.

The person who has had a synovectomy of the knee would be encouraged to move the knee as frequently as possible. This is often difficult because of pain, and a person oftentimes requires the encouragement, support and reinforcement of a therapist who can tell them how the knee is moving, help them by controlling the situation and documenting their progress.

The electromechanical hinge device would be supplied to the patient and once instructed, they could apply it to themselves, so that during the course of the day, they would perform repetitively attempts at full extension and full flexion.

As with other types of knee difficulties, the knee will want to rest in a comfortable degree of flexion. This is oftentimes at approximately 35 degrees. A person with the electromechanical hinge device in place would attempt to extend the knee as much as possible and the device would read back to them how extension of the knee is progressing, whether it is reaching 15, 12, or 10 degrees, as they attempt to regain extension, or whether they are able to reach 90, 100, 120 degrees as they attempt to flex the knee. The patient would receive direct measured feedback through the devices readout of how their motion is progressing. The device would also control the extremity for them. It would give them the encouragement and feedback that they need to get that last degree or two. This type of encouragement does tend to result in more cooperation of the patient and more strenuous effort, and ultimately, more success with such therapy. Over a course of several days, a few degrees extra each day would result in continued improvement, whereas, without the device the patient is more likely not only to not gain the extra few degrees but to lose degrees as the knee, rested inappropriately, gets stiff.

In summary, the patient who has used he electromechanical hinge will have a safe, effective method of supervision, reinforcement, and documentation as they pursue motion for stiffness following synovectomy for rheumatoid arthritis.

XI. ANTERIOR CRUCIATE LIGAMENT REPAIR WITH A PRE-DETERMINED SAFE ARC OR MOTION WITH A SEPARATE SAFE ARC OF STRENGTHENING

A person who has undergone an anterior cruciate repair is allowed to move their knee within a prescribed range of motion. Usually this is between 45 and 90 degrees of flexion. A person is kept out of more flexion or more extension (by active muscle contraction), because this will strain or pull against the repair.

The electromechanical hinge could be applied to such a person's knee with benefit for two main reasons:

(1) It would monitor their motion within the prescribed flexion arc so that they would not actively attempt to extend the knee outside that arc. The hinge could be set to prevent this motion.

(2) It could monitor the quadriceps and hamstring muscle contractions to determine whether or not an unacceptable degree of force is being transmitted across the knee (which could harm the repair).

The electromechanical hinge would be applied to the knee in the following way. The hinged device would be applied to the knee with the knee at some resting degree of flexion, perhaps at 35 degrees. This is considered to be a safe and comfortable resting point following such a surgery.

The patient when reminded by the device, could release the locking device, place their knee in the prescribed free range, between 45 and 90 degrees, and attempt to exercise it. They could attempt to exercise the knee (if this was considered safe by the surgeon) against infinite resistance at 45 degrees and at 90 degrees or at other points on the star hinge. The hinge could be locked by a time release mechanism. If difficulty is encountered moving the knee in this flexion arc, the device would monitor the improvement in flexion (by reinforcing them with. a direct digital readout) until endpoint (and infinite) resistance is reached. At that endpoint, the isometric contraction would begin and the patient's strengthening will be monitored much as it would be for an instrumented cast.

The person using such a device would benefit from it in the following ways:

(1) The knee could be protected in the prescribed flexion arc and they would be allowed in a supervised way (supervised by the machine) to exercise it. This should obviate some of the need for direct physical therapy intervention.

(2) The patient would benefit from strengthening the muscles in isometric contraction at the two or more points allowed by the locking hinge. In this example, there would be an isometric contraction at 45 and 90 degrees but the star hinge concept may allow them to do resistance at not only 45 and 90 degrees, but also 60 and 70 degrees. The person therefore coming but of such a device once it is safe to move the knee in a greater degree of flexion would have more strength and be more easily able to do so.

(3) A person using the device would be more likely to get the surgeon's desired degree of mobility earlier, since it would be in a controlled and managed fashion.

(4) This brace could be their post-operative brace instrumented in such a way that it could be applied by the surgeon for direct control immediately.

Preferably, some type of device to monitor translation of the tibia could be incorporated so that, if the repair is stressed, this device could alarm the patient.

AUGMENTING DEVICES

PROPOSED METHODS OF USE

FIVE-YEAR-OLD WITH LONG OBLIQUE FRACTURE OF DISTAL TIBIA, WEIGHT BEARING DISALLOWED

A child with a long oblique fracture of the distal tibia is a special problem since the child will not or cannot obey a medical instruction to protect the tibia against unwanted weight bearing. Shortening or deformity can result. Such a fracture is ordinarily treated in a long leg cast but cannot prevent the child from placing unwanted weight on the extremity.

A weight bearing alarm mechanism comprising a standard commercial load cell interconnected with a control unit including an alarm device is incorporated into the restraining device with the load cell located on the bottom of the cast or perhaps across the ankle so that a child bearing weight on the cast would be personally notified by some type of audible or palpable signal. Additionally, digital memory in the control unit records the number of infractions which occur for later feedback to the physician. This may be useful information in determining methods of treatment (altering the cast or the child's mobility), degree of healing and relative stability (an undisplaced fracture after multiple infractions and, in fact, be proven to be stable).

The physician and the patient would benefit from the use of an alarm mechanism to monitor a cast in a child with a long oblique fracture of the tibia in the following way:

The compliance of the individual is monitored and direct evidence is available to the physician as to whether or not further changes in the treatment program are necessary and whether or not compliance with the plan is present.

TIME RELEASE MECHANISM FOR RANGE OF MOTION CONTROL

A person who has undergone anterior cruciate reconstruction or other types of ligament surgery about the knee is allowed only a certain degree of movement immediately after the surgery. The amount of movement allowed at the knee is gradually increased until the patient is approaching near full extension and near full flexion at 6–12 weeks post surgery.

There has always been some confusion as to exactly how fast the patient may progress. there is not a lot of literature data to support exactly what degree of freedom will protect the repair. Most orthopedists doing this type of surgery do believe that active extension against resistance near full extension may disrupt the repair, so most surgeons do not allow this initially.

The proposed augmentation of the electromechanical hinge device includes a time release mechanism such that a computer control unit interconnected with the electromechanical hinge would, with its internal clock, allow 45–90° of flexion, let's say, at one week; 35–90° at two weeks; 25–90° of flexion at three weeks; and so on until the patient gradually reaches full extension.

At the present time the patient with such a hinge must report to the doctor's office to have the hinges adjusted, and sometimes this results in rather marked limitation in a patient's ability to move the knee. For example, a patient may go from an allowable flexion arc of 45–90° to an allowable flexion arc of 15–90° at two or three weeks. This sudden release of the knee from such constraints is uncomfortable and the patient is pushing against more stiffness than if the knee had been allowed to release gradually. This results in a certain degree of discomfort.

A person with a time release hinge would be benefited in the following ways:

(1) An electromechanically hinged brace would be applied to the knee following ligament reconstruction surgery, with the physician's desired protocol for motion programmed into the control unit of the brace.

(2) The brace would allow the patient to move the knee in the desired flexion arc immediately after surgery. Alternately or preferably, the brace may be locked by the time mechanism initially so that the patient may have comfort during the early post-operative period when pain is most acute.

(3) The patient would be discharged from the hospital and the knee motion would be gradually regained at the expected rate by the surgeon's instructions as it is programmed into the brace. The patient may then be able to maintain contact with the physician over the phone, discussing how the motion is progressing within the brace, having direct digital readout and feedback through the computerized device.

(4) The patient would have, at the end of the period of immobilization, a more limber knee, a more efficient period of immobilization.

(5) The patient would probably have less discomfort since the allowable motion is returned to the knee gradually.

During the course of immobilization in the incrementally adjustable hinge, whether or not controlled by the timing mechanism, the patient may be able to lock their knee at various degrees of flexion, perhaps at 15 degree intervals, so that they can perform isometric contraction, gaining strength within the allowable flexion arc. This would be an application of the incrementally adjustable hinge concept within the electromechanical hinge concept. A combination of the incrementally adjustable hinge concept, the electromechanical hinge concept and the timing mechanism concept would be greatly advantageous to such a patient. their pursuit of strength and motion would be optimized within the constraints of the needed immobilization and protection.

INSTRUMENTED BRACE

PROPOSED METHOD OF USE

A STRENGTHENING DEVICE FOR A TORSO TO BE USED WITH LOW BACK, UPPER BACK OR ABDOMINAL MUSCULAR WEAKNESS

A person who has low back weakness is often asked to exercise the abdominal and spinal musculature to provide coordination and stabilizing effects on the spine. Many patients find this difficult because of the attendant pain which may be present in the presence of a compression fracture, degenerative disc disease, spinal arthritis or general debility following an injury.

A person would apply a brace to himself which would restrict motion in forward flexion and side bending, and the brace would be instrumented with strain gauges along its members, such that a person attempting to flex at the waist, for example, would be restrained from doing so (to prevent the motion which is often painful), but. the strength in attempts at flexion could be monitored to document the degree of effort exhibited and the compliance over time. For example, a patient would apply the brace in an attempt to perform 15 flexion exercises at the waist, 15 extension exercises (where they attempt to lift the chest, let's say, off of the bed in a prone position), 15 side bending exercises to the left and 15 side bending exercises to the right. They would be reminded to execute the protocol, possibly by an alarm mechanism on the brace (if the brace were to be worn full-time), or by some other type of reminding device (if the brace was not indicated for continued wear). This would depend upon the patient's specific need and determination by the surgeon.

A person using such a device would benefit in the following ways:

(1) They would be able to safely and reliably use the device.

(2) They would be able to safely and reliably exercise their back in a protected fashion, even when no motion is allowed. This may allow certain individuals otherwise unable to exercise to do so in a controlled fashion. Isometric exercise, though perhaps not as beneficial as certain types of isotonic or dynamic resistance exercise, is preferable over no exercise at all.

(3) The patient's progress in strength, endurance and compliance could be monitored. The absolute strength could be monitored by the strain gauge, their endurance could be monitored by their ability to hold a forceful contraction over time. Their compliance could be monitored by measuring actual number of repetitions, number of days continued exercises, etc.

In summary, then, a patient using such an isometric conditioning device for the torso should be able to benefit by improvement in both strength and motion. The physician should be able to benefit by obtaining useful monitoring of the patient's improvement as it affects both objective and subjective parameters.

It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of shape, size and arrangement of parts within the principles of the present invention to the full extent indicated by the broad general meaning of the terms in which the appended claims are expressed.

What is claimed is:

1. A method of optimizing isometric exercises comprising:

(a) engaging first and second flexibly connected body portions of the individual in an orthopedic restraining device having at least one strain gauge;

(b) designing a target exercise routine based on the physical condition of the patient;

(c) monitoring the exercise activities of the individual from the reading of the strain gauge; and (d) determining the deviation of the actual exercise routine from the target routine.

* * * * *